United States Patent
Garcia-Bengochea et al.

(10) Patent No.: US 8,152,714 B2
(45) Date of Patent: Apr. 10, 2012

(54) CURVILINER SPINAL ACCESS METHOD AND DEVICE

(75) Inventors: Javier Garcia-Bengochea, Jacksonville, FL (US); Jeffrey Allen Guyer, Cardiff By the Sea, CA (US); Thomas Purcell, Del Mar, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 1074 days.

(21) Appl. No.: 12/069,721

(22) Filed: Feb. 11, 2008

(65) Prior Publication Data
US 2008/0221586 A1 Sep. 11, 2008

Related U.S. Application Data

(60) Provisional application No. 60/900,554, filed on Feb. 9, 2007.

(51) Int. Cl.
*A61B 17/02* (2006.01)
*A61B 17/34* (2006.01)
(52) U.S. Cl. ................ 600/114; 606/86 A
(58) Field of Classification Search ............ 600/114, 600/184; 606/86 A, 246
See application file for complete search history.

(56) References Cited

U.S. PATENT DOCUMENTS

| | | | |
|---|---|---|---|
| 4,545,374 A | 10/1985 | Jacobson | 128/303 |
| 5,540,687 A | 7/1996 | Fairley et al. | 606/60 |
| 5,762,629 A * | 6/1998 | Kambin | 604/164.11 |
| 6,063,088 A | 5/2000 | Winslow | 606/61 |
| 6,162,170 A | 12/2000 | Foley et al. | |
| 6,206,826 B1 | 3/2001 | Mathews et al. | 600/210 |
| 6,267,763 B1 | 7/2001 | Castro | 606/61 |
| 6,283,966 B1 | 9/2001 | Houfburg | 606/61 |
| 6,514,260 B1 | 2/2003 | Zdeblick et al. | 606/90 |
| 6,520,967 B1 | 2/2003 | Cauthen | 606/99 |
| 6,540,753 B2 | 4/2003 | Cohen | 606/90 |

(Continued)

FOREIGN PATENT DOCUMENTS

WO    WO 97/29680    8/1997

(Continued)

OTHER PUBLICATIONS

International Search Report for Application No. PCT/US2008/001856 dated of mailing May 23, 2008.

*Primary Examiner* — Ralph Lewis
(74) *Attorney, Agent, or Firm* — Michael R. Shevlin

(57) ABSTRACT

A curvilinear spinal access device for performing a procedure on a spine of a patient is disclosed. The device includes a working portal configured to be advanced toward a surgical site located at the spine of the patient. The working portal includes a distal end and a proximate end, a working portal housing having an open interior channel disposed between the distal end and the proximate end, an exterior channel disposed on an outside surface of the working portal housing and between the distal end and the proximate end. The distal end is configured to be disposed at the surgical site and the proximate end is disposed away from the surgical site. The housing has a curved shape defined between the proximate end and the distal end, wherein the proximate end is disposed with respect to the distal end. The working channel is configured to allow advancement of at least one surgical tool and/or at least one implant toward the surgical site.

18 Claims, 23 Drawing Sheets

U.S. PATENT DOCUMENTS

| | | | |
|---|---|---|---|
| 6,565,574 B2 | 5/2003 | Michelson | 606/90 |
| 6,575,981 B1 | 6/2003 | Boyd et al. | 606/90 |
| 6,595,995 B2 | 7/2003 | Zdeblick et al. | 606/80 |
| 6,648,895 B2 | 11/2003 | Burkus et al. | 606/90 |
| 6,666,891 B2 | 12/2003 | Boehm et al. | 623/17.16 |
| 6,709,438 B2 | 3/2004 | Dixon et al. | 606/90 |
| 6,730,126 B2 | 5/2004 | Boehm, Jr. et al. | 623/17.15 |
| 6,743,234 B2 | 6/2004 | Burkus et al. | 606/90 |
| 6,755,839 B2 | 6/2004 | Van Hoeck et al. | 606/87 |
| 6,814,737 B2 | 11/2004 | Cauthen | 606/99 |
| 6,851,430 B2 * | 2/2005 | Tsou | 128/898 |
| 6,896,680 B2 | 5/2005 | Michelson | 606/90 |
| 6,986,772 B2 | 1/2006 | Michelson | 606/90 |
| 7,074,226 B2 | 7/2006 | Roehm, III et al. | 606/90 |
| 7,108,698 B2 | 9/2006 | Robbins et al. | 606/90 |
| 7,118,579 B2 | 10/2006 | Michelson | 606/90 |
| 7,137,985 B2 | 11/2006 | Jahng | 606/61 |
| 7,153,304 B2 | 12/2006 | Robie et al. | 606/90 |
| 7,153,305 B2 | 12/2006 | Johnson et al. | 606/90 |
| 7,166,073 B2 | 1/2007 | Ritland | 600/210 |
| 7,169,152 B2 | 1/2007 | Foley et al. | 606/90 |
| 7,179,263 B2 | 2/2007 | Zdeblick et al. | 606/90 |
| 7,189,242 B2 | 3/2007 | Boyd et al. | 606/90 |
| 7,226,451 B2 | 6/2007 | Shluzas et al. | 606/86 |
| 7,241,297 B2 | 7/2007 | Shaolian et al. | 606/80 |
| 7,244,258 B2 | 7/2007 | Burkus et al. | 606/90 |
| 7,252,673 B2 | 8/2007 | Lim | 606/99 |
| 7,311,713 B2 | 12/2007 | Johnson et al. | 606/90 |
| 7,314,468 B2 | 1/2008 | Michelson | 606/90 |
| 7,320,686 B2 | 1/2008 | Serhan et al. | 606/90 |
| 2002/0013588 A1 | 1/2002 | Landry et al. | 606/99 |
| 2002/0107574 A1 | 8/2002 | Boehm, Jr. et al. | 623/17.16 |
| 2002/0128659 A1 | 9/2002 | Michelson | 606/90 |
| 2002/0156481 A1 | 10/2002 | Boyd et al. | 606/90 |
| 2002/0193802 A1 | 12/2002 | Zdeblick et al. | 606/96 |
| 2003/0083688 A1 | 5/2003 | Simonson | |
| 2003/0176926 A1 | 9/2003 | Boehm, Jr. et al. | 623/17.16 |
| 2003/0195520 A1 | 10/2003 | Boyd et al. | 606/90 |
| 2004/0024408 A1 | 2/2004 | Burkus et al. | 606/90 |
| 2004/0097932 A1 | 5/2004 | Ray, III et al. | 606/61 |
| 2004/0133201 A1 | 7/2004 | Shluzas et al. | 606/61 |
| 2004/0176775 A1 | 9/2004 | Burkus et al. | 606/90 |
| 2004/0181233 A1 | 9/2004 | Michelson | 606/90 |
| 2005/0159650 A1 | 7/2005 | Raymond et al. | 600/201 |
| 2005/0165405 A1 | 7/2005 | Tsou | |
| 2005/0171541 A1 | 8/2005 | Boehm, Jr. et al. | 606/61 |
| 2005/0171551 A1 | 8/2005 | Sukovich et al. | 606/86 |
| 2005/0203625 A1 | 9/2005 | Boehm, Jr. et al. | 623/17.11 |
| 2006/0030850 A1 | 2/2006 | Keegan et al. | 606/60 |
| 2006/0052793 A1 | 3/2006 | Heinz | 606/90 |
| 2006/0069404 A1 | 3/2006 | Shluzas et al. | 606/198 |
| 2006/0111728 A1 | 5/2006 | Abdou | 606/86 |
| 2006/0116688 A1 | 6/2006 | Boyd et al. | 606/90 |
| 2006/0149278 A1 | 7/2006 | Abdou | 606/90 |
| 2006/0149279 A1 | 7/2006 | Matthews | 606/90 |
| 2006/0200139 A1 | 9/2006 | Michelson | 606/61 |
| 2006/0200164 A1 | 9/2006 | Michelson | 606/90 |
| 2007/0055272 A1 | 3/2007 | Schaller | 606/90 |
| 2007/0055274 A1 | 3/2007 | Appenzeiler et al. | 606/90 |
| 2007/0173831 A1 | 7/2007 | Abdou | 606/61 |
| 2007/0233083 A1 | 10/2007 | Abdou | 606/61 |
| 2007/0270873 A1 | 11/2007 | Flickinger et al. | 606/90 |
| 2007/0299444 A1 | 12/2007 | DiPoto et al. | 606/61 |

FOREIGN PATENT DOCUMENTS

| | | |
|---|---|---|
| WO | WO 2006/041963 A2 | 4/2006 |
| WO | WO 2006/089085 A2 | 8/2006 |
| WO | WO 2008/058070 A2 | 5/2008 |

* cited by examiner

CURVILINER SPINAL ACCESS METHOD AND DEVICE

CROSS-REFERENCE TO RELATED APPLICATIONS

The present application claims priority to U.S. Provisional Application No. 60/900,554, to Garcia-Bengochea, filed Feb. 9, 2007, and titled "Guided Lumbar Interbody Fusion Method and System" and incorporates its entire disclosure hereby by reference.

BACKGROUND OF THE INVENTION

1. Field of the Invention

This invention relates generally to the field of spinal surgery. In particular, the present invention relates to the field of surgical access to the spine.

2. Background of the Invention

Surgical techniques that are considered to be minimally invasive utilize instrumentation and implant design that allow the site to be prepared and the implant to be introduced through one or several small incisions in the patient. For example, in the lumbar spine, surgical procedures known as lumbar interbody fusion ("LIF") have become common over the past ten years. Particular techniques are typically designated by the direction of approach relative to the spine—anterior ("ALIF"), posterior ("PLIF"), transverse ("TLIF"), and extreme lateral ("XLIF"). While these procedures are an improvement over conventional surgery in that muscular disruption and trauma are minimized, difficulties in the techniques have limited widespread adoption in the medical community.

For example, anterior approaches require the use of an access surgeon in addition to the spinal surgeon to navigate through the abdomen and require mobilization of the abdominal viscera and great vessels. Anterior approaches also do not safely allow for revision or re-exploration and can incur additional complication such as ileus and abdominal pain. Should further fixation be required these approaches do not allow posterior fixation without repositioning the patient. This procedure is commonly called a 360 operation where the operation begins with the patient in the supine position for the ALIF procedure and then flipped, re-sterilized and posterior fixation is applied with the patient in the prone position. These procedures increase the time of the operation which directly relates to blood loss, recovery time and hospital fees.

Posterior and transverse approaches provide some advantages over anterior approaches, yet still require some exposure of the nerves or thecal sac, making placement of large (and therefore more stable) implants difficult. Therefore posterior and transverse approaches require the use of fixation devices that are smaller than those used in anterior approaches.

Extreme lateral approaches still provide some advantages over previously discussed procedures yet require cumbersome positioning, long operating distances and provide no access to the spinal canal. In these approaches the patient is placed on their side which allows a larger access area to implant a bigger device but does not overcome the setback of repositioning the patient should posterior fixation be required. Thus, there is a need for a minimally invasive method and device that allows access to the lateral spine while the patient is placed in a prone position. This configuration would be advantageous because it also allows posterior access without repositioning the patient should posterior fixation be required. Disclosed herein is a specialized curvilinear device and method wherein the lateral spine is access through a curved access portal which may or may not comprise a slot/rail combination.

SUMMARY OF THE INVENTION

The present invention is directed to a device and a methodology for access to the spine, including devices and methodologies in the lumbar interbody fusion ("LIF") field, that address some of the actual or perceived problems with other known spinal access procedures. The present invention's equipment and implant design enable the present invention's procedure, which allows an advantageous access to the spine.

In some embodiments, the techniques disclosed herein are directed to a semi-automated posterior approach to perform a lateral spinal procedure, such as discectomy, bony removal, tissue removal, implant placement and/or fusion. In some embodiments, the present invention relates to a method and instrumentation for performance of the method, wherein the pathway or approach to the spine is through curved portals of varying angles.

The instrumentation for performance of the procedure is curved, allowing the procedure to be performed on a prone patient. In this manner, the approach to the spine is initially posterior and finally lateral or transverse at the spine, the arc in the instrumentation altering the direction of approach approximately about 45 to about 90 degrees, alternately about 55 to about 80 degrees, alternately about 65 to about 75 degrees, within the body. The instrumentation is inserted through a small incision located laterally from the spinal midline a distance approximately equal to the distance from the center of the vertebral body to just outside the skin. A rail/slot combination in a curved portal is provided such that instrumentation and the implant remain oriented in the proper direction during insertion. A representative portal may have an inner diameter of approximately 22 mm, with the rail or slot having a depth or diameter of approximately 3 mm. Those skilled in the art will recognize that the portal does not have to be circular.

In some embodiments, the device will comprise an implant. When used, the implant possesses a curved longitudinal axis and curved side walls matching that of the portal and other instrumentation. The implant can also include a slot or rail that cooperates with a rail or slot of the portal such that the implant remains in a controlled orientation during insertion. Multiple embodiments for the implant are possible, such as bone screws, plates, interbody devices, and/or artificial discs. While dimensions will vary dependent on the size of the patient, a representative implant may have a height ranging from approximately 8 to 18 mm, an anterior-posterior depth of approximately 22 mm and a lateral width of approximately 45 to 55 mm.

In some embodiments, additional instrumentation such as trocars, dilators and guides that possess a circular, rectangular or elliptical cross-section. The guide rail or slot in the portal can be configured in such fashion that instrumentation used subsequent to positioning of the portal are each provided corresponding slots or rails that allow for relative telescoping or axial movement between the instrumentation and the guide retractor, such instrumentation including an annulotomy chisel, a disc whisk, and the implant inserter.

Some of the objects and advantages of the present invention include: providing an approach to the spine maintaining the patient in a prone position and avoiding complications of other approaches discussed above; allowing multiple procedures and treatments in the operating room without repositioning the patient; providing a larger sized, more stable implant previously not availably implanted from a posterior angle; and allowing implantation of supplemental instrumentation posteriorly.

The conventional LIF procedures relate to direct, linear approaches, whereas the present invention's procedure provides for a curvilinear guided approach. In some embodiments, instrumentation can be configured to have arced longitudinal axes, allowing the patient to be positioned prone for the operation. This is the most natural position for spinal surgery, allowing for posterior decompression and surgical manipulation through the same surgical field without the need to reposition the patient or the need for an access surgeon. Additionally, the present invention's approach direction adjacent to the spine being transverse allows relatively unimpeded access to the surgical area where a large implant or instrumentation may be utilized.

In some embodiments, the present invention relates to a device for performing an interbody fusion procedure on the spine of a patient. The device includes a working portal configured to be advanced toward a surgical site located at the spine of the patient. The working portal includes a distal end and a proximate end, a working portal housing having an open interior channel disposed between the distal end and the proximate end. The working portal can also include an exterior channel disposed on an outside surface of the working portal housing and between the distal end and the proximate end. The distal end is configured to be disposed at the surgical site and the proximate end is disposed away from the surgical site. The housing has a curved shape defined between the proximate end and the distal end. In some embodiments, the proximate end is disposed substantially perpendicularly with respect to the distal end. The working channel is configured to allow advancement of at least one surgical tool and/or at least one implant toward the surgical site. In other embodiments, the present invention relates to a guided lumbar interbody fusion ("GLIF") device for performing a procedure on a vertebral disc of a spine of a patient. In other embodiments, the procedure can be used to perform neural decompression, total disc arthroplasty, and/or nucleus replacement, among other spinal surgical procedures.

In some embodiments, the present invention relates to a method for performing an interbody fusion procedure on the spine of a patient. The method includes advancing a working portal toward a surgical site located at the spine of the patient. The working portal includes a distal end and a proximate end, a working portal housing having an open interior channel disposed between the distal end and the proximate end. The working portal can also include an exterior channel disposed on an outside surface of the working portal housing and between the distal end and the proximate end. The distal end is configured to be disposed at the surgical site and the proximate end is disposed away from the surgical site. The housing has a curved shape defined between the proximate end and the distal end, wherein the proximate end is disposed substantially perpendicularly with respect to the distal end. The method further includes advancing at least one surgical tool and/or at least one implant toward the surgical site via the working channel to perform the procedure. In some embodiments, the present invention relates to a method for performing a guided lumbar interbody fusion ("GLIF") procedure on a vertebral disc of the spine of a patient.

Further features and advantages of the invention, as well as structure and operation of various embodiments of the invention, are disclosed in detail below with references to the accompanying drawings.

BRIEF DESCRIPTION OF THE DRAWINGS

The present invention is described with reference to the accompanying drawings. In the drawings, like reference numbers indicate identical or functionally similar elements. Additionally, the left-most digit(s) of a reference number identifies the drawing in which the reference number first appears.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The following description provides a general overview of the concepts discussed in the present application. Additional embodiments are discussed below with regard to FIGS. 1-44c.

The procedure begins with placing the patient in a prone position and arranging the proper drapery to establish proper sterilization of the operation site. Next, the surgeon uses a measuring device to measure a specified distance from the midline. At this point, the surgeon will make a mark using some marking device as a reference point to create an incision. The specified distance can be calculated using a chart or sliding scale that determines the appropriate distance to make the incision. This distance is directly related to the distance of the center of the vertebral body to the flat surface of the patient's back; given this distance along with the known arc angle of the portal and known center of the midline, the incision distance can be properly calculated.

Figure 28:
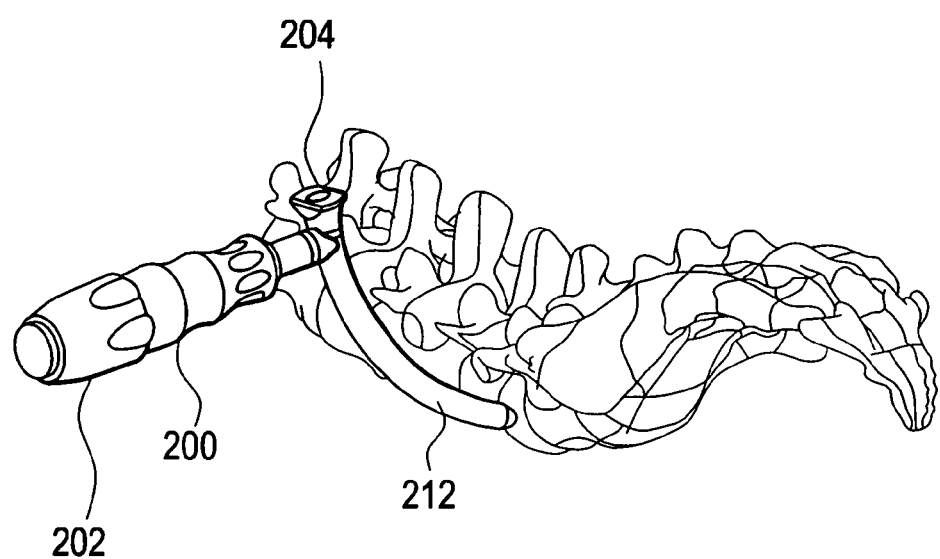
FIG. 28 illustrates an exemplary usage of the trocar guide to reach a "50-yard line" of a vertebral disc, according to some embodiments of the present invention.

An incision is created at the marked point and the surgeon performs blunt dissection with a finger to estimate retroperitoneal space ("RPS") and tissue, such as the psoas muscle. Then, the trocar guide is advanced over the finger of the surgeon into the tissue splitting the fibers vertically until it abuts the spine on the centerline of the vertebral body (as shown in FIG. 28). Positioning of the trocar guide is confirmed with x-ray. The trocar guide has a curved body that has an inner cannulated channel and an offset handle. The instrument may have a small "tooth" on the inner wall to engage the spine and hold it in place. A neurophys stylette can be put in the trocar guide through this process to safely monitor potential nerve disruption. Once successful docking is achieved and the optional neurophys is acceptable, the neurophys stylette is removed.

A cutting trocar of similar shape and size as the neurophys stylette with a sharp tip is then passed through the cannulated channel in the trocar guide to pierce the spine. To facilitate better control, the trocar handle can be applied to the cutting trocar. A mallet may also be used to advance the cutting trocar. The cutting trocar is then removed and replaced with the barbed trocar which is similarly sized and has a blunt tip and barbed features to anchor the trocar. The trocar handle can be similarly applied to facilitate handling of the barbed trocar. The barbed trocar can be "tapered" or "notched" so that the anatomy "grabs" the barbed features. The trocar handle is removed from the trocar and the trocar guide can be removed.

The tissue separator is followed down the length of the barbed trocar to the lateral surface of the spine, such as the vertebral disc annulus. The device is actuated to "peel" tissue, such as muscle, off the spine and prepare the surgical site for further instrumentation, similar to periostial elevators. In some embodiments, a ringed handle is contracted and expanded to create a sweeping motion of a blade at the end of the tissue separator instrument. This blade can be of teardropped shape to better facilitate insertion and removal of the device with minimal anatomic disruption and can be bifurcated to enable "peeling" of the tissue above and below the trocar without removing the instrument to "peel" above then reinserting to "peel" below the trocar. There can also be features to help maintain the instrument along the trocar. The tissue separator is then removed.

The tissue distracters are then assembled in the tissue distracter alignment block so that the ends of the tissue distracters are together. The tissue distracters are curved instruments of suitable material and geometry to move anatomy without harming or otherwise disrupting the patient's internals. The tips of the tissue distracters contain a lip of approximately 5 mm in order to "catch" the tissue along the spine and maintain positioning against the lateral wall of the spine. The tips of the tissue distracters can also be tapered to aid in insertion. The opposite ends of the tissue distracters have geometry to interact with the alignment block. This end also has outwardly curved geometry to facilitate the later part of the procedure. The dorsal tissue distracter can have neurophys in the form of a cable or ribbon to help monitor nerve disruption during installation and through the remainder of the operation. To aid in keeping this assembly together, an elastic polymer sheath can be slipped over assembly before insertion. The alignment block is removed.

The small dilator is then pushed between outwardly curved geometry through the tissue distracters and over the barbed trocar until it abuts the lateral wall of the spine. This procedure in turn expands the distance between the tissue distracters. A second large dilator is then followed in a similar fashion to further distract tissue distracters. Though only two dilators are described in the above embodiment, more sequential smaller dilators can be used. The dilators are created in such fashion that they are consecutively smaller in length so that the end part from the preceding dilator protrudes from the subsequent dilator to aid in the later removal. Finger notches can be added for better grip while insertion and removal. Through this process the sheath aids in preventing tissue creep between tissue distracters.

The curved portal is then passed over the largest dilator between the tissue distracters. Proper location is verified and adjusted using X-ray and endoscopic visualization. Once proper location is achieved, the anterior awl is passed through a channel in the curved portal to firmly "dock" the assembly to the annulus. Further, a stabilization arm can be applied to a boss feature off the curved portal. At this point, the barbed trocar and dilators can be removed. The portal is securely docked and ready to begin the technique.

In some embodiments, to safely guide the portal to the surgical site, the curved portal has slots and/or rails that interact with preceding instrumentation that also includes corresponding slots and/or rails. Examples of the preceding instrumentation include, but are not limited to, trocars, tissue distracters, and/or dilators.

Specialized curved instrumentation, inserted through the curved portal, is then used to complete the surgical procedures. In some embodiments, this instrumentation can have slots and/or rails which interact with the curved portal to safely guide instrumentation to the surgical site. In at least one embodiment, these procedures include removing the annulus, cleaning and preparing the disc space, inserting and securing the implant. In these embodiments, instrumentation can include an annulotomy knife, disc whisk, curettes, chisels, implant trials and curved inserting devices. In the embodiments where an implant is used in the procedure, proper location of the implant is then confirmed via x-ray. Finally, the curved portal and tissue distracters are removed to complete the procedure. Posterior fixation can be then begin, if needed.

The following is a more detailed description of the exemplary interbody fusion procedure and instrumentation with regard to FIGS. 1-44*c*, according to some embodiments of the present invention. In some embodiments, the present invention relates to a guided lumbar interbody fusion procedure and instrumentation.

Figure 1:
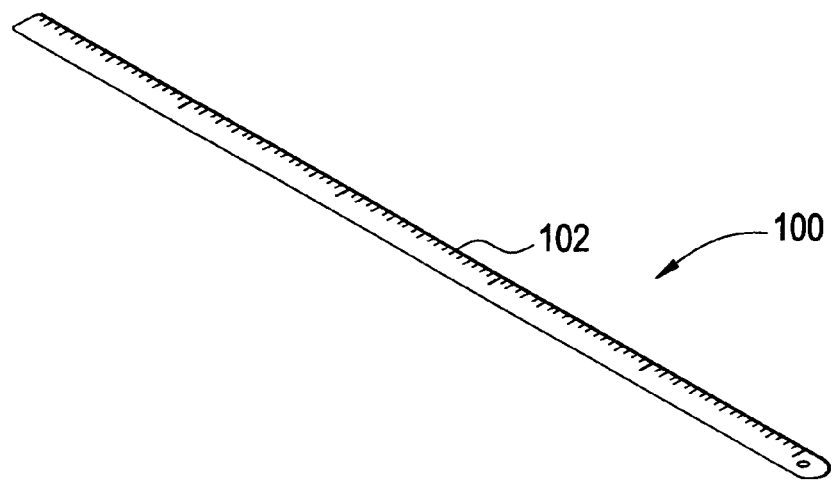
FIG. 1 illustrates an exemplary measuring device with cutout designations for locating a point of entry for delivering of instrumentation, according to some embodiments of the present invention.

FIG. 1 illustrates an exemplary measuring device 100 for locating a point of entry for delivering of instrumentation, according to some embodiments of the present invention. In some embodiments, the measuring device 100 can be a ruler. In some embodiments, the measuring device 100 can be a straight x-ray ruler with cutout designations 102 that include notches that can be seen in a fluoroscopy image.

Figure 27:
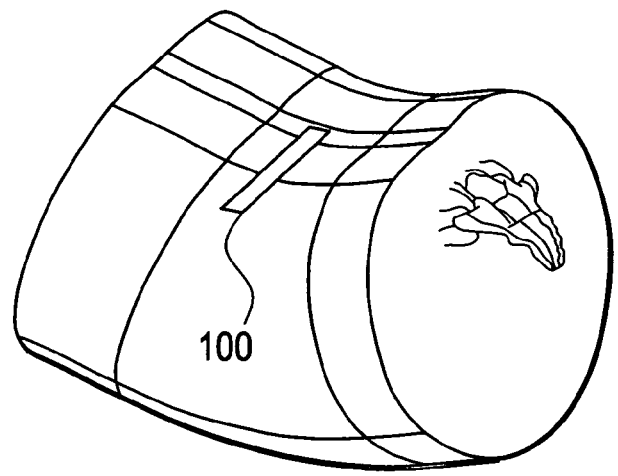
FIG. 27 illustrates an exemplary way of measurement from the midline of patient in order to locate incision, according to some embodiments of the present invention.
Figure 43:
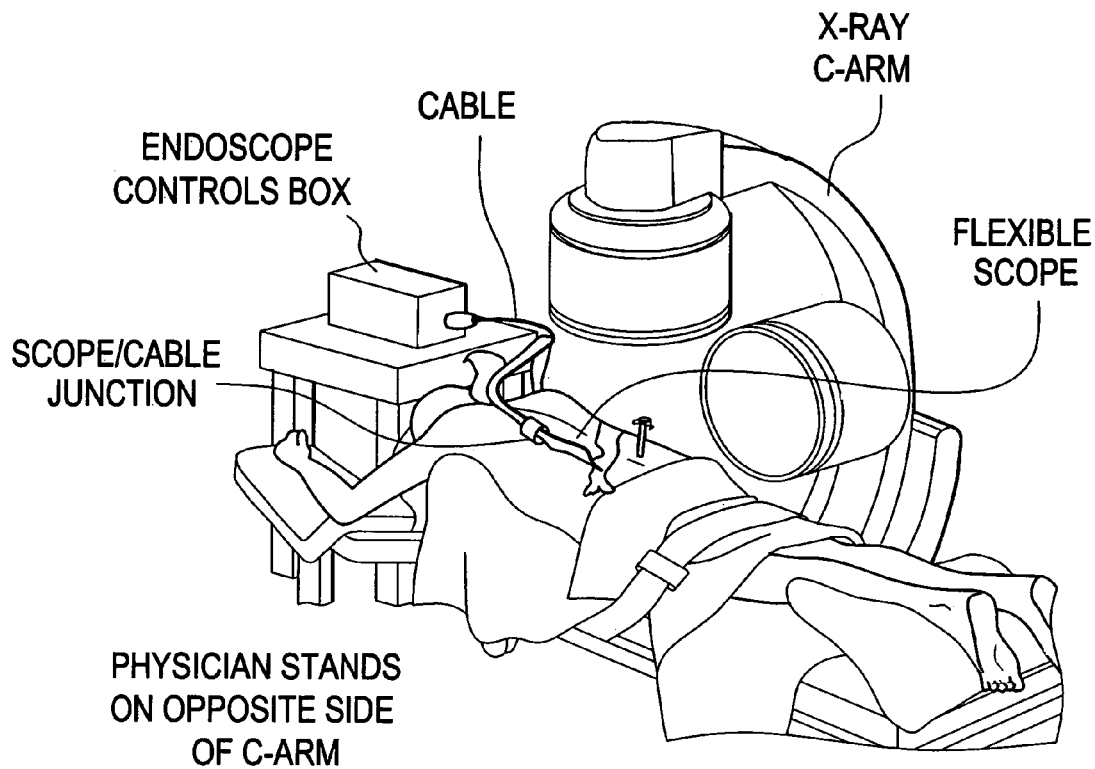
FIG. 43 illustrates a patient in a prone position for performance of the disclosed procedure, according to some embodiments of the present invention.

To perform the procedure, the patient is placed in a prone position, as illustrated in FIG. 43. Using the measuring device 100, the surgeon measures a specified distance from the midline of the back of the patient, as shown in FIG. 27. Once the measurement is made, the surgeon makes a mark using a marking device as a reference point to create an incision. In some embodiments, the incision can be about 4 to about 50 millimeters ("mm") wide. In some embodiments, the surgeon can use a chart, a sliding scale or any other methodology to determine location of the incision and the width of the incision. In some embodiments, based on this determination, the surgeon can also decide as to the angle of the portal through which the surgery will be performed.

Figure 2:
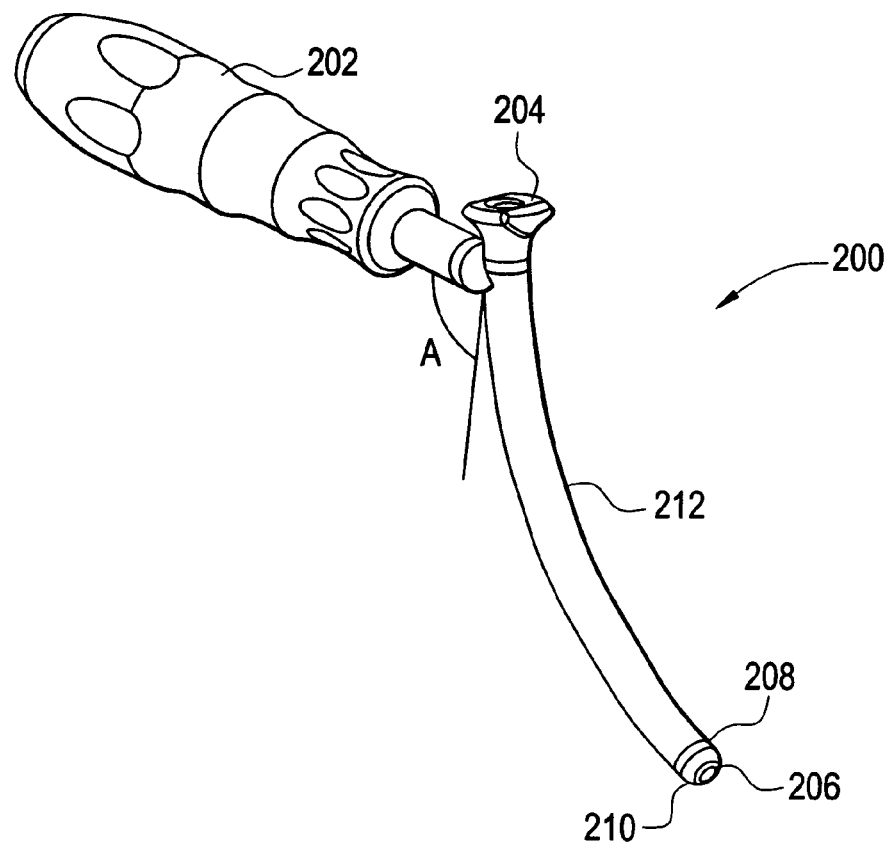
FIG. 2 illustrates an exemplary trocar guide, according to some embodiments of the present invention.
Figure 3:
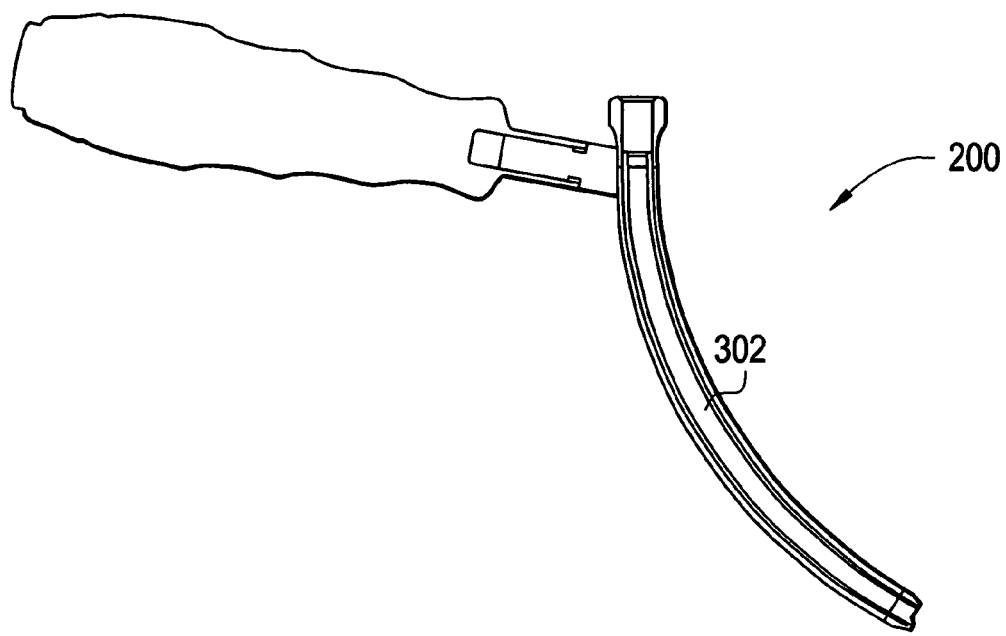
FIG. 3 is a cross-sectional view of the trocar guide shown in FIG. 2 that illustrates a curved channel for accepting a trocar or a neuro-monitoring stylette, according to some embodiments of the present invention.

FIG. 2 illustrates an exemplary trocar guide 200, according to some embodiments of the present invention. FIG. 3 is a cross-sectional view of the trocar guide 200 shown in FIG. 2 that illustrates a curved channel 302 for accepting a trocar or a neuro-monitoring stylette, according to some embodiments of the present invention. The trocar will be further discussed below with regard to FIG. 4.

During the procedure, the surgeon uses the trocar guide 200 and a dissecting finger to navigate through soft tissue, such as the fascia and psoas muscles of the patient, as shown in FIG. 28. The trocar guide 200 includes a handle 202 and a shaft 212. The shaft 212 includes a proximal end 204 and a distal end 206. The proximal end 204 includes a flat surface that the surgeon can use to hammer in the trocar guide 200. The distal end 206 further includes a tip 208 that can be configured to include a neuro-monitoring element. The distal end 206 also includes a rasping surface 210 to help anchor against lateral wall of the spine. In some embodiments, the angle A that is formed between the plane of the handle and the plane that is perpendicular to the flat surface at the proximal end 204 is approximately 100 degrees. As can be understood by one skilled in the art, angle A can have any other value. In some embodiments, the handle 202 can be manufactured from silicone and can be further configured to comfortably guide the proximal end of the instrument to the centerline of the vertebral body. As can be understood by one skilled in the art, other materials can be used for the handle 202.

The trocar guide 202 includes a channel 302 that is configured to accommodate placement of the trocar or a stylette. The channel 302 is disposed inside the shaft 202 and is configured to track the curvature of the trocar guide's shaft 202. Such curved channel 302 allows insertion of a curved trocar (as shown in FIGS. 4-5).

Figure 4:
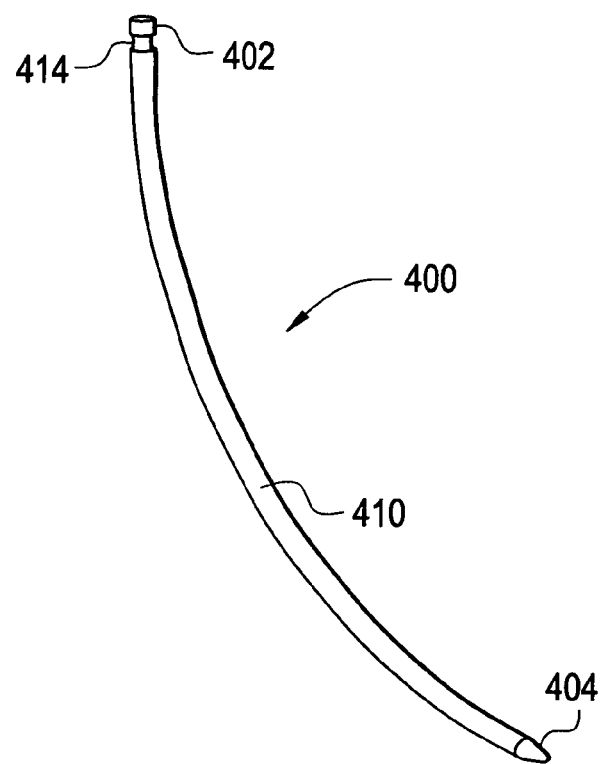
FIG. 4 illustrates an exemplary cutting trocar, according to some embodiments of the present invention.
Figure 5:
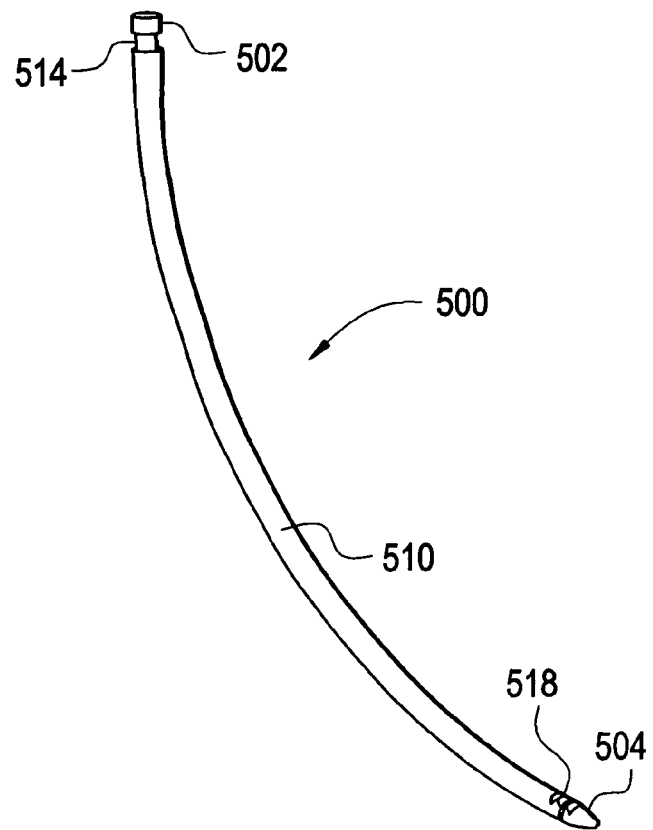
FIG. 5 illustrates an exemplary barbed/docking trocar, according to some embodiments of the present invention.

FIGS. 4-5 illustrate various exemplary trocars, according to some embodiments of the present invention.

Figure 29:
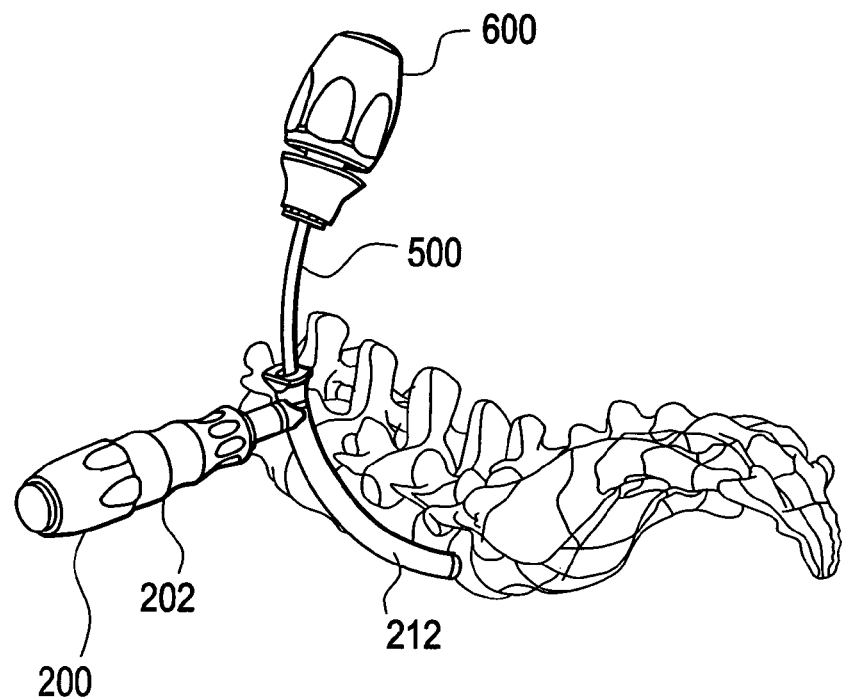
FIG. 29 illustrates the trocar with handle traveling through channel in the trocar guide, according to some embodiments of the present invention.

FIG. 4 illustrates an exemplary cutting trocar, according to some embodiments of the present invention. The cutting trocar 400 includes a distal end 402, a proximate end 404 and a shaft 410 disposed between the distal end 402 and the proximate end 404. The shaft 410 is configured to be curved in a similar fashion as the trocar guide 200. The proximate end 404 includes a pointed tip. The distal end 402 can be configured to include a grooved portion 414 that allows the handle 600 to be secured to the trocar 400. The cutting trocar 400 (shown in FIG. 4) is inserted down the trocar guide's channel 302 (shown in FIG. 3) in order to make an incision or initial punch into the vertebral wall of the patient. Then, the cutting trocar 400 is removed from the channel 302 and a barbed trocar 500 (shown in FIG. 5) is inserted, as shown in FIG. 29.

Figure 30:
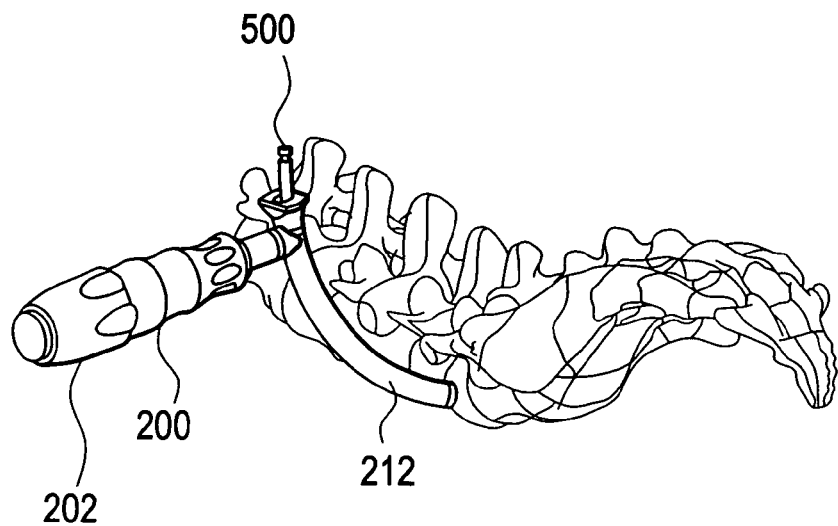
FIG. 30 illustrates the docked trocar with handle removed through trocar guide, according to some embodiments of the present invention.
Figure 31:
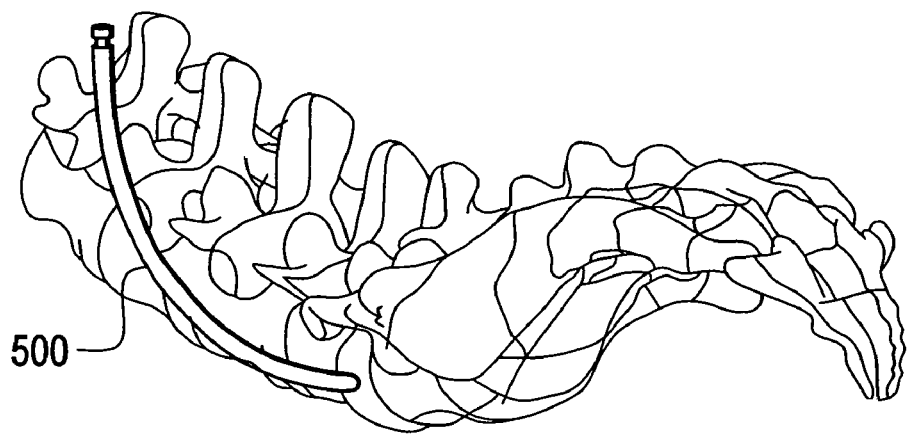
FIG. 31 illustrates the docked trocar with trocar guide removed, according to some embodiments of the present invention.

FIG. 5 illustrates an exemplary barbed/docking trocar, according to some embodiments of the present invention. The barbed trocar 500 includes a distal end 502, a proximate end 504, a shaft 510 disposed between the distal end 502 and the proximate end 504. The shaft 510 is configured to be curved in a similar fashion as the trocar guide 200. The proximate end 504 includes a pointed tip and barbs 518 that can be configured to secure the barbed trocar 500 to the spine. Similar to the trocar 400, the distal end 502 of the trocar 500 can be configured to include a grooved portion 514 that allows the handle 600 to be secured to the trocar 500. The barbed trocar is inserted down the trocar guide channel 302 (shown in FIG. 3) in order to mount to the lateral wall of the spine to provide a guide to the surgical site. Once the barbed trocar 500 is secured to the vertebral wall, a handle 600 (shown in FIGS. 6-8) is removed from the barbed trocar 500, thereby leaving the barbed trocar 500 secured to the spine, as shown in FIG. 30. The trocar guide 200 is then removed from the incision, as shown in FIG. 31.

Figure 6:
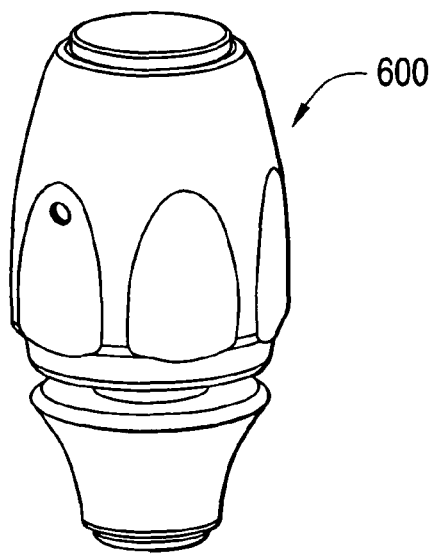
FIG. 6 illustrates an exemplary trocar handle, according to some embodiments of the present invention.
Figure 7:
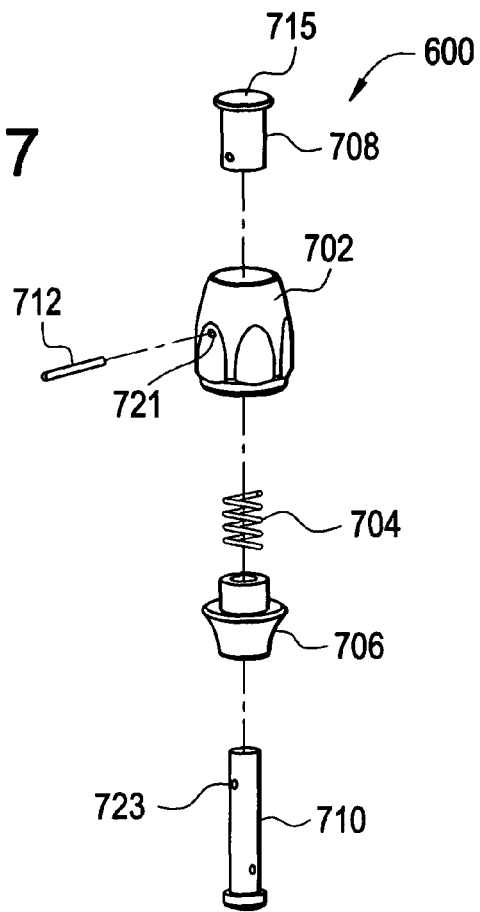
FIG. 7 is an exploded view of the trocar handle shown in FIG. 6.
Figure 8:
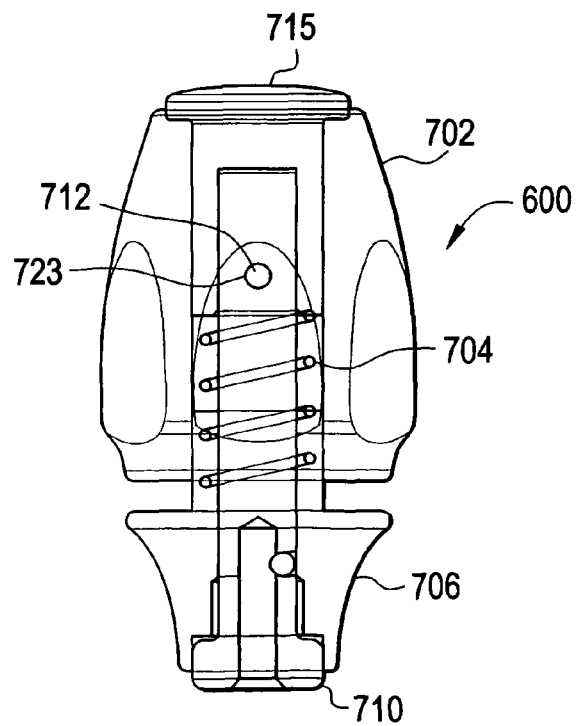
FIG. 8 is a sectional view of the trocar handle shown in FIG. 6.

FIGS. 6-8 illustrate an exemplary handle 600, according to some embodiments of the present invention. FIG. 6 illustrates the assembled trocar handle 600. FIG. 7 is an exploded view of the trocar handle shown in FIG. 6. FIG. 8 is a sectional view of the trocar handle shown in FIG. 6.

Referring to FIG. 7, the trocar handle 600 includes a handle portion 702, spring 704, bottom portion 706, a top portion 708, a shaft 710, and a locking pin 712. The handle portion 702 can be configured to be manufactured from silicon or any other suitable material(s). The top portion 708 includes a hardened surface 715. The surgeon can use surface 715 to hammer in the trocars 400 and 500. In some embodiments, the surface 715 can be manufactured from any metal or any other suitable material(s). In some embodiments, the spring 704 can be configured to control locking of the components within handle portion 702.

The handle portion 702 includes an opening 721. The shaft 710 includes an opening 723. The openings 721, and 723 are configured to be sized to accommodate insertion of the locking pin 712. The shaft 710 is configured to be inserted through the bottom portion 706, the spring 704, the handle portion 702, and the top portion 708. Once all the portions are assembled together, the locking pin 712 is inserted to secure the handle 600 together, as illustrated in FIGS. 6 and 8.

Figure 10:
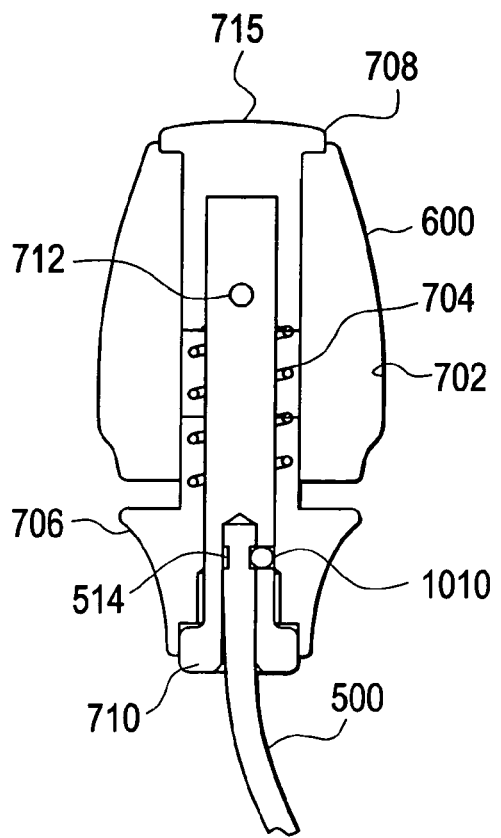
FIG. 10 is detailed sectional view of the trocar/trocar handle interaction, according to some embodiments of the present invention.

Referring to FIGS. 7 and 10, the shaft 710 of the handle 600 includes a hollow interior configured to accommodate placement of the trocar. The shaft 710 further includes a locking pin 1010 that is configured to interact with the grooves 514 of the trocar 500 and lock the trocar 500 inside the shaft 710. By squeezing the bottom portion 706, the locking pin 1010 is shifted and the trocar 500 is released from the shaft 710. As can be understood by one skilled in the art, other ways of securing the trocar 500 inside the handle 600 are possible.

Figure 9:
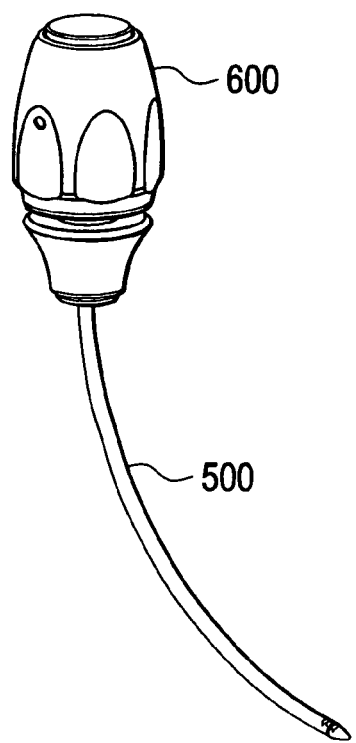
FIG. 9 illustrates the trocar handle loaded with the trocar, according to some embodiments of the present invention.

FIG. 9 illustrates the trocar handle loaded with the barbed trocar 500. FIG. 10 is detailed sectional view of the trocar 500 and trocar handle 600 interaction, according to some embodiments of the present invention. As can be understood by one skilled in the art, trocar 400 can also be loaded into the handle 600 in the same fashion as the trocar 500.

Figure 11:
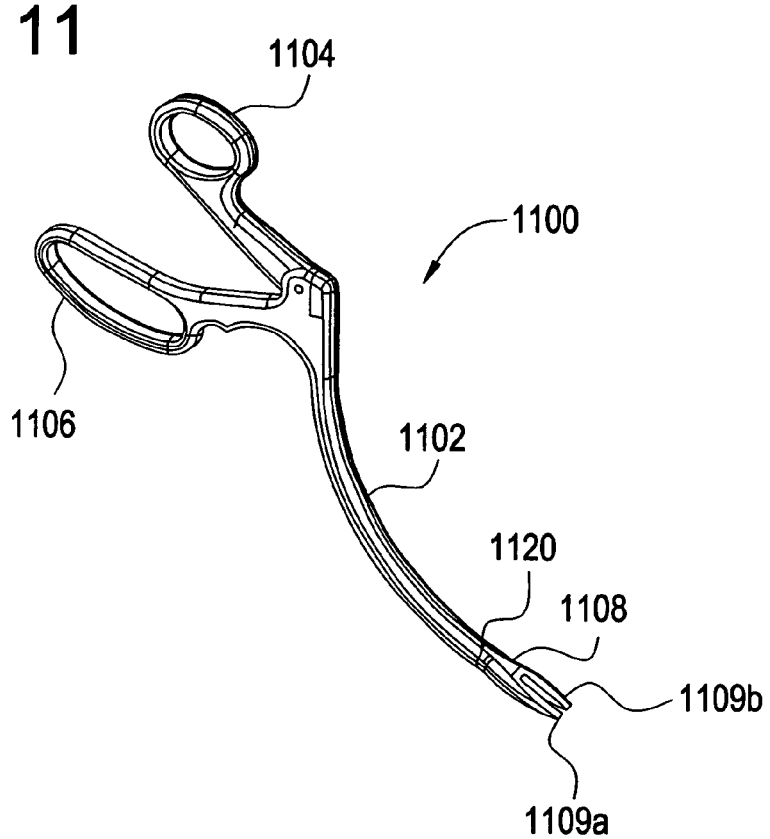
FIG. 11 illustrates an exemplary tissue separator, according to some embodiments of the present invention.
Figure 12:
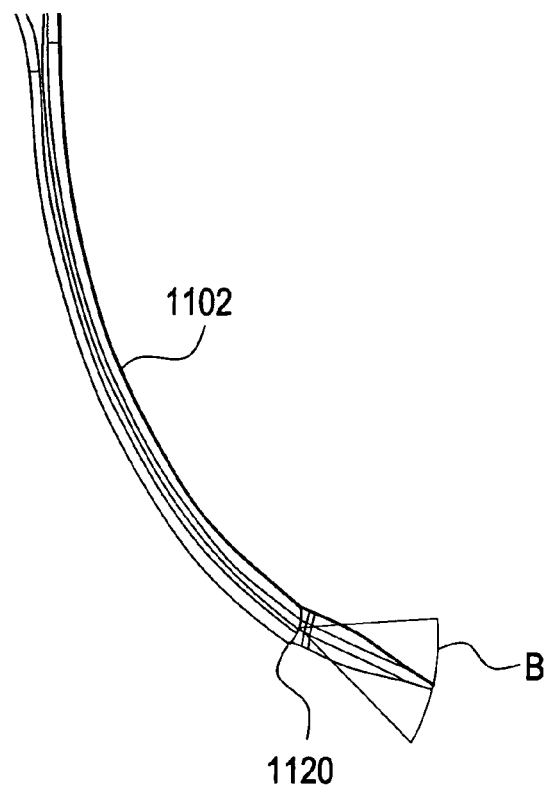
FIG. 12 illustrates exemplary working aspects of the tissue separator, according to some embodiments of the present invention.
Figure 13:
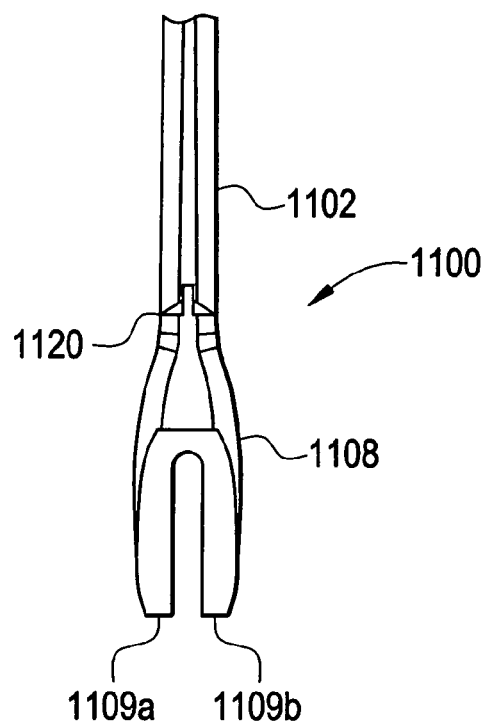
FIG. 13 illustrates the tear-drop working end geometry of the tissue separator shown in FIG. 11.
Figure 14:
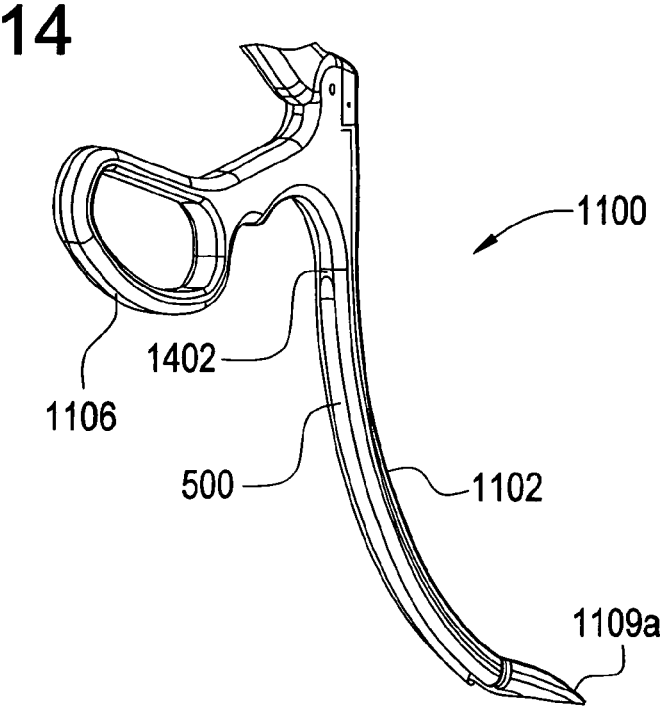
FIG. 14 illustrates an exemplary trocar channel cutout on the underside of the tissue separator, according to some embodiments of the present invention.
Figure 32:
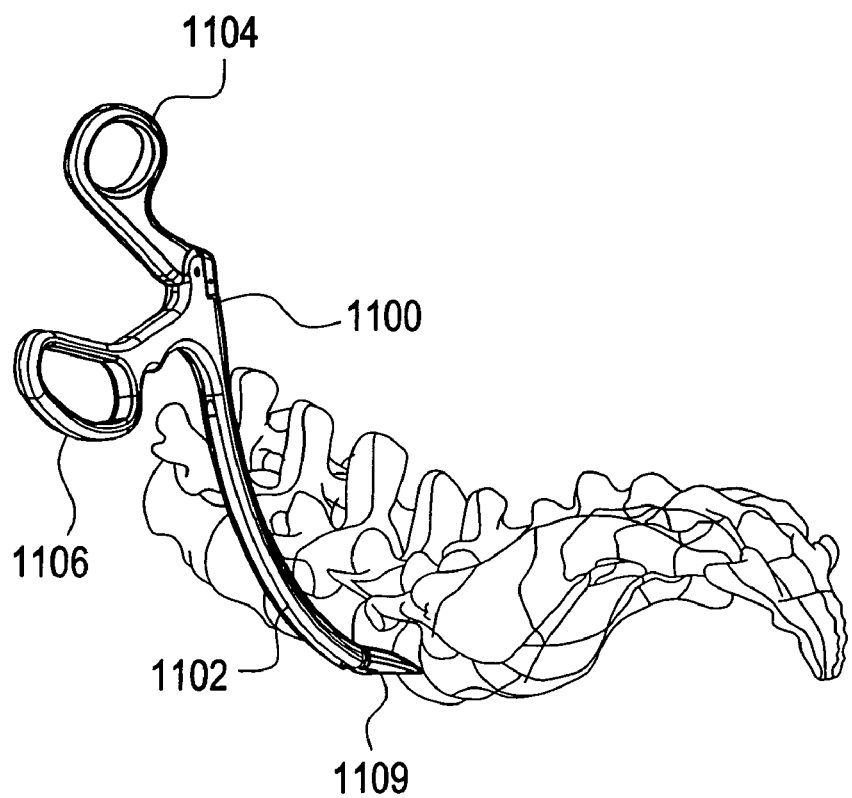
FIG. 32 illustrates the tissue separator traveling the length of the trocar to an operating site, where the tear drop end will sweep approximately 12 mm above and below trocar, according to some embodiments of the present invention.

FIGS. 11-14 illustrate an exemplary tissue separator 1100, according to some embodiments of the present invention. FIG. 11 is a general view of the tissue separator 1100. FIG. 12 illustrates exemplary working aspects of the tissue separator 1100, according to some embodiments of the present invention. FIG. 13 illustrates the tear-drop working end geometry of the tissue separator 1100. FIG. 14 illustrates an exemplary trocar channel cutout 1402 on the underside of the tissue separator 1100. The tissue separator 1100 is guided down the barbed trocar 500 (shown in FIG. 5) to the vertebral wall and is actuated to separate tissue from the vertebral wall, as illustrated in FIG. 32. The trocar channel cutout on the underside of the tissue separator can be used to aid in guiding the tissue separator down the barbed trocar. In some embodiments, the tissue can be separated above the trocar and then separated below the trocar.

The tissue separator 1100 includes a shaft 1102, handles 1104, 1106, distal portion 1108 have separators 1109a and 1109b. The handles 1104, 1106 are hingedly coupled to the shaft 1102 at the pivotal connection 1120. The handles 1104, 1106 are configured to control movement of the separators 1109a, 1109b. The shaft 1102 is configured to have a similar curved geometry as the trocar guide 200, as shown in FIG. 2. The separators 1109 (a, b) are configured to remove or peel tissue at the location of the docked barbed trocar 500 (shown in FIG. 5). Such removal is possible through up and down pivotal movement B as illustrated in FIG. 12. In some embodiments, the movement B is possible through rotational motion of the handles 1104, 1106 in a scissor like fashion. In some embodiments, one of the handles 1104, 1106 (e.g., 1106) can be fixedly secured to the shaft 1102, whereas the other handle (e.g., 1104) can be configured to rotate. Those skilled in the art will recognize that other actuation methods for this device can be used.

In some embodiments, the distance between separators 1109a and 1109b can be configured to accommodate the diameter of the trocar 500. The tissue separator 1100 can be configured to be slid down the trocar 500 using channel 1402 (illustrated in FIG. 14). The channel 1402 is configured to be disposed on the back side of the tissue separator 1100 and allows the surgeon to guide the tissue separator 1100 to remove tissue(s) surrounding the trocar 500. The removal is accomplished through pivotal movement of the separators 1109(a, b). In exemplary embodiments of spinal surgery procedures, the tissue separator 1100 can be used to separate psoas muscle tissue. As can be understood by one skilled in the art, the separator 1100 can be used for any other tissue separation and/or removal.

Figure 15:
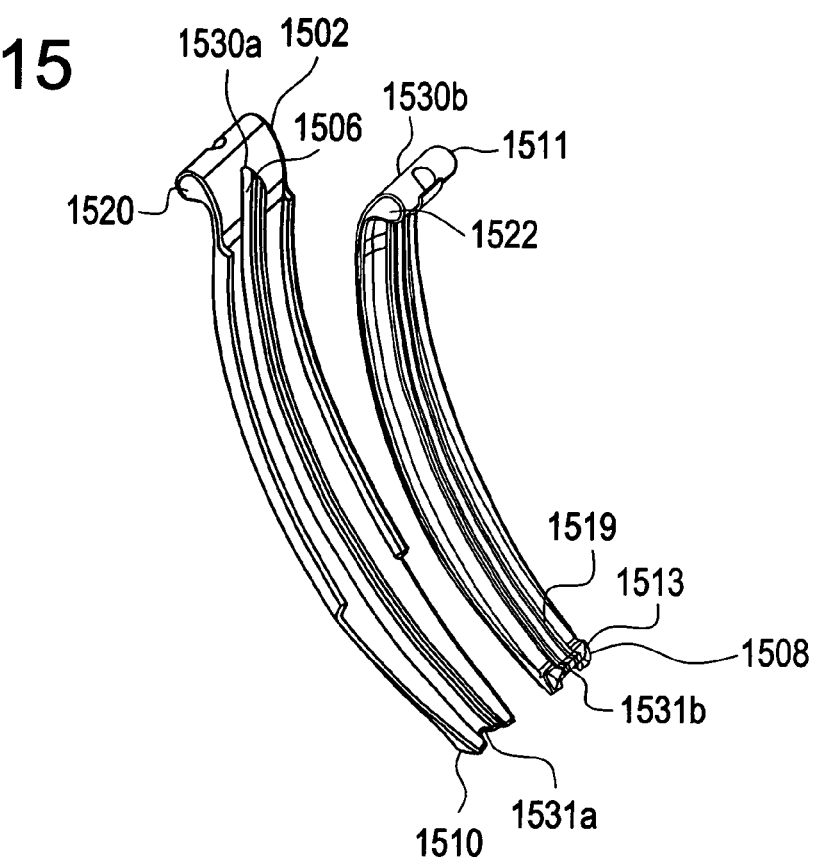
FIG. 15 illustrates exemplary anterior and dorsal tissue distracters, according to some embodiments of the present invention.
Figure 16:
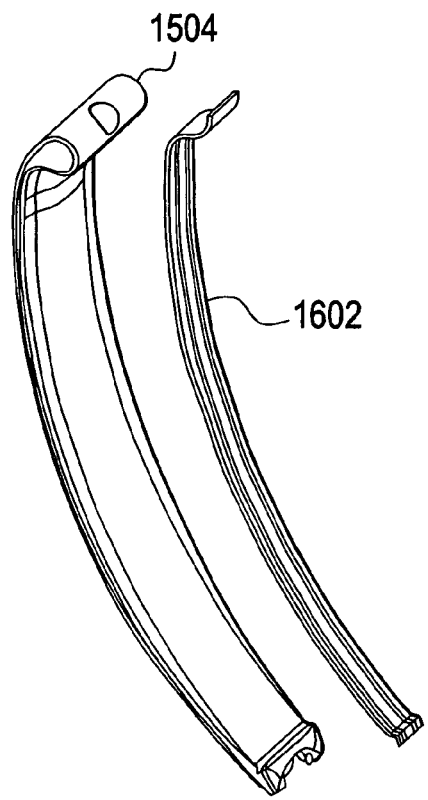
FIG. 16 illustrates an exemplary assembly of a neuro monitoring ribbon installed on the dorsal tissue distracter shown in FIG. 15, according to some embodiments of the present invention.

FIG. 15 illustrates an exemplary anterior tissue distracter 1502 and dorsal tissue distracter 1504, according to some embodiments of the present invention. FIG. 16 illustrates an exemplary assembly of a neuro monitoring ribbon 1602 installed on the dorsal tissue distracter 1504, according to some embodiments of the present invention. The distracters can be also referred to as distraction ramps. In some embodiments, the distracters can be delivered as a single unit along the inserted barbed trocar 500 (shown in FIG. 5), where the trocar 500 is placed between the distracters, to the vertebral wall. In some embodiments, the distraction ramps 1502, 1504 are delivered together as a single unit in a balloon, which keeps the ramps joined and prevents encroachment of soft tissue between the ramps.

Referring to FIG. 15, the ramp 1504 will be discussed. The structure of the ramp 1502 is similar to the ramp 1504. The ramp 1504 includes a proximal end 1511 and a distal end 1513. The ramp 1504 further includes a rail/slot (shown as rail/slot 1506 on ramp 1502). The rail/slot 1506 is configured to be disposed on the interior side of the ramps 1502 and 1504 and further configured to accommodate guiding of instruments (such as trocars or dilators) down to the procedure working area at the surgical site. The rail/slot on each ramp is disposed between the proximal and distal ends and is further configured to create openings 1530 at the proximal end 1511 (formed by two rail/slot portions 1530a and 1530b) and 1531 (formed by two portions 1531a and 1531b) at the distal end 1508 of the ramps, when the ramps' interior sides are joined together. As stated above, such openings are configured to accommodate placement of instruments between the ramps.

At the distal end 1508, the ramp 1504 further includes a lip 1513 (the ramp 1502 includes a lip 1510) that is configured to help navigate through the soft tissue and "grab" the tissue. As the ramps are guided down the barbed trocar 500, the lip 1513 (and/or lip 1510) on the ramp are configured to push away the tissue allowing the ramps to approach the wall of the vertebral disc. In some embodiments, the ramps include a monitoring element 1602 disposed on the ramp 1504 (also referred to as a dorsal ramp), as illustrated in FIG. 16. In some embodiments, the monitoring element 1602 can be configured to be any conventional neural monitoring element that allows detection of approaching neural tissue via application of current. In some embodiments, the element 1602 can be configured to be coupled to an electrical supply (not shown) that delivers current to the tissue via element 1602 and upon detection of a response, the element 1602 can determine whether neural tissue is proximate to the element 1602 and/or the ramp 1504 (and/or 1502). Further, the neuron-monitoring element 1602 can be used to preserve the integrity of neural structures and provide an early detection to prevent or minimize damage to those structures during surgical procedures. As can be understood by one skilled in the art, both ramps 1502 and 1504 can be configured to include element 1602.

Figure 17:
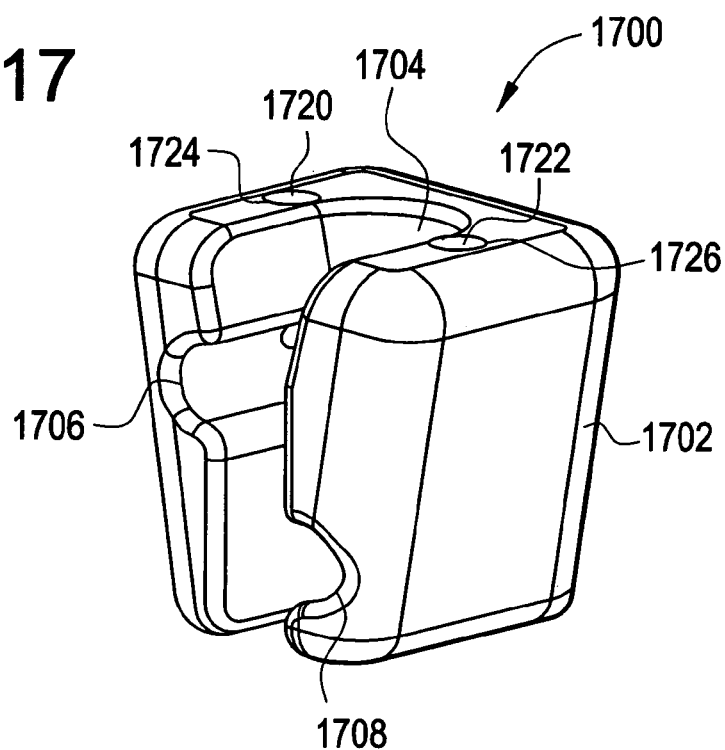
FIG. 17 illustrates an exemplary tissue distracter alignment block, according to some embodiments of the present invention.
Figure 18:
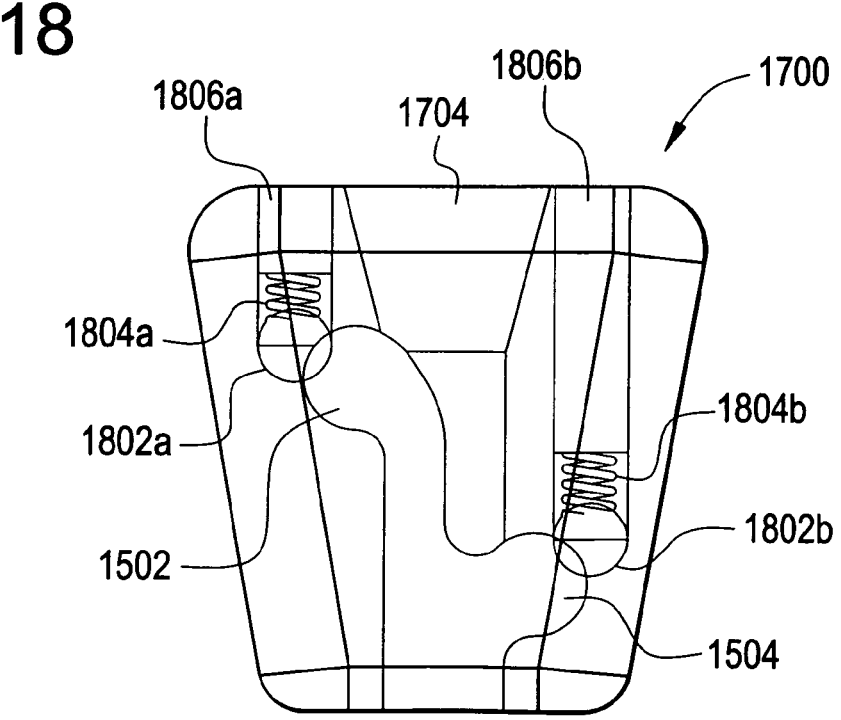
FIG. 18 illustrates an exemplary cutout for receiving tissue distracters and exemplary internal components of a spring ball detents that lock the tissue distracters, according to some embodiments of the present invention.
Figure 19:
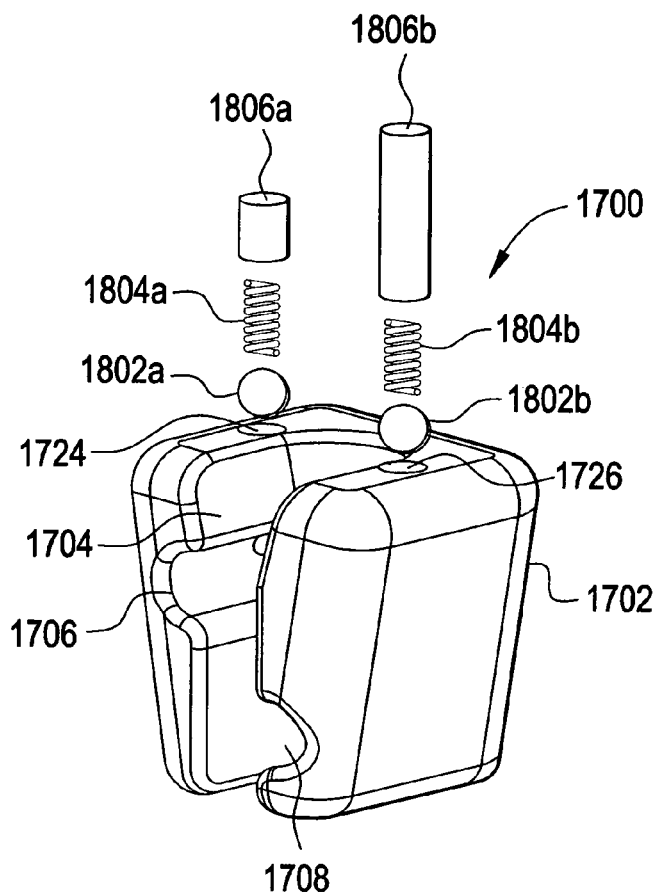
FIG. 19 is an exploded view of the tissue distracter alignment block, according to some embodiments of the present invention.
Figure 20:
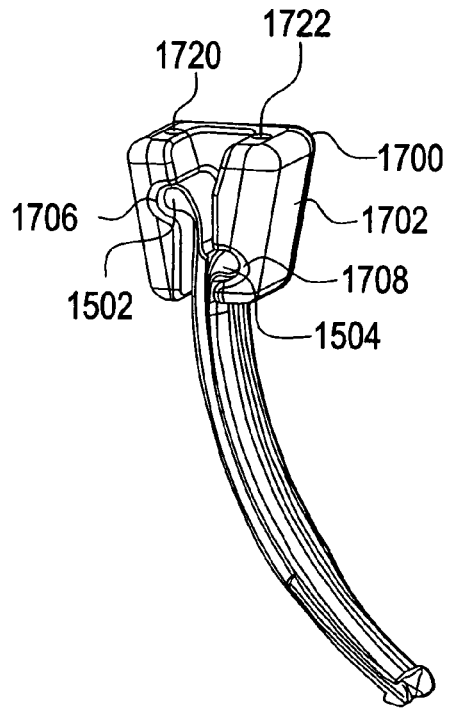
FIG. 20 illustrates an exemplary way of fitting the tissue distracters inside the alignment block, according to some embodiments of the present invention.
Figure 33:
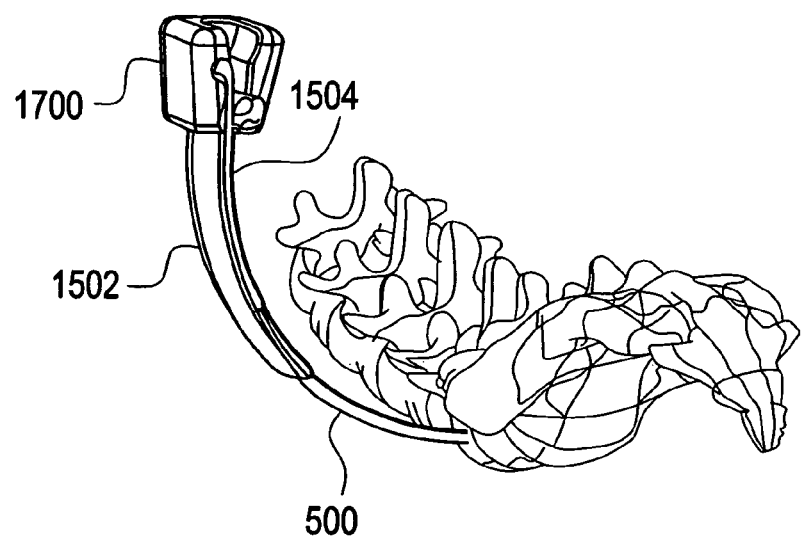
FIG. 33 illustrates tissue distracters with alignment block traveling the length of the trocar to the operating site, according to some embodiments of the present invention.

In some embodiments, the distraction ramps 1502 and 1504 can have variable lengths and a distracter alignment block 1700, illustrated in FIG. 17, can be used to align the ramps 1502 and 1504 for proper insertion and approach to the surgical site (as shown in FIG. 33). FIGS. 18-20 are various views of the distracter alignment block 1700. FIG. 18 is a cross-sectional view of the block 1700 showing tissue distracters and internal components of block 1700 that include a spring ball detents that lock the tissue distracters, according to some embodiments of the present invention. FIG. 19 is an exploded view of the tissue distracter alignment block 1700. FIG. 20 illustrates an exemplary way of fitting the tissue distracters inside the alignment block 1700.

Referring to FIG. 17, block 1700 includes a housing 1702 having an open channel 1704 disposed inside the housing 1702. The open channel 1704 is further configured to be disposed between the top and the bottom of the housing 1702. The channel 1704 includes grooves 1706 and 1708 disposed on each side of the open channel 1704, as shown in FIG. 17. The grooves 1706 and 1708 are configured to accommodate placement of the proximal ends of the distraction ramps 1502 and 1504, respectively. Referring to FIGS. 15 and 17, the proximal ends of the ramps 1502, 1504 include protruding portions that are configured to be curved away from their interior portions and are sized to fit inside the open channel 1704 and the grooves 1706 and 1708, respectively. In some embodiments, the ramps 1502, 1504 can be configured to be inserted into the channel 1704 simultaneously or one after the other. Since, the channel 1704 is open on one side of the housing 1702 and closed on the other side of the housing 1702, the ramps 1502, 1504 are prevented from sliding out after being inserted into the grooves 1706, 1708. To further prevent the ramps 1502, 1504 from sliding out the open side of the channel 1704, locking mechanisms 1720, 1722, respectively. The locking mechanisms 1720, 1722 are configured to be disposed within the openings/holes 1724, 1726, respectively, which are further accessible through the top of the housing 1702 of the block 1700, as illustrated in FIG. 17.

Figure 34:
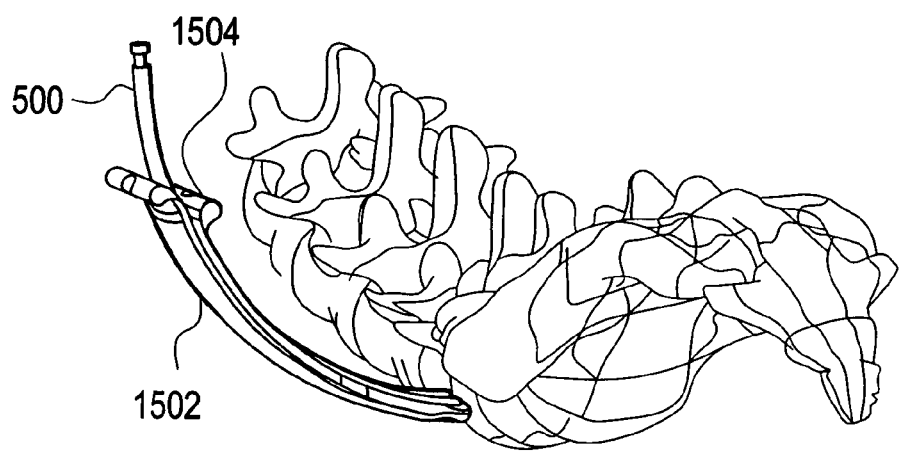
FIG. 34 illustrates tissue distracters being fully inserted, according to some embodiments of the present invention.

Referring to FIGS. 18 and 19, the locking mechanisms 1720, 1722 are illustrated in further detail. Each one of the locking mechanisms 1720, 1722 includes a ball 1802 (*a*, *b*,), a spring 1804 (*a*, *b*), and a locking pin 1806 (*a*, *b*). The balls 1802 are configured to be inserted first into the openings 1724, 1726, followed by the spring 1804, and then pins 1806. In some embodiments, the pin 1806*a* is configured to be shorter than the pin 1806*b* since the groove 1708 is disposed lower than the groove 1706 along the open channel 1704. The pins 1806 can further include a locking device that prevents the pins from accidentally falling out of the openings 1724, 1726. Upon insertion of the balls 1802, springs 1804, and pins 1806 into the openings 1724, 1726, respectively, and insertion of the ramps 1502, 1504 into the grooves 1706, 1708, respectively, the balls 1802 upon being pushed by the pins 1806 via springs 1804, push on the protrusions of the ramps 1502, 1504, which secures the ramps 1502, 1504 inside the grooves 1706, 1708. This locking arrangement prevents accidental slippage of the ramps 1502, 1504 and allows proper insertion and advancement of the ramps toward the vertebral wall of the disc. FIG. 20 illustrates the ramps 1502, 1504 being secured inside the alignment block 1700. In some embodiments, the channel 1704, disposed on the interior portion of the housing 1702, is configured to be wider near the top of the housing 1702 and narrower near the bottom of the housing 1702, as illustrated in FIG. 20. This allows to further secure the ramps 1502, 1504 inside the housing 1702. Once the ramps are advanced toward the surgical site, the alignment block can be removed to allow tissue distraction, which can be accomplished using distraction ramps 1502, 1504, and insertion of dilators (discussed below with regard to FIGS. 21-22), as shown in FIG. 34.

Figure 21:
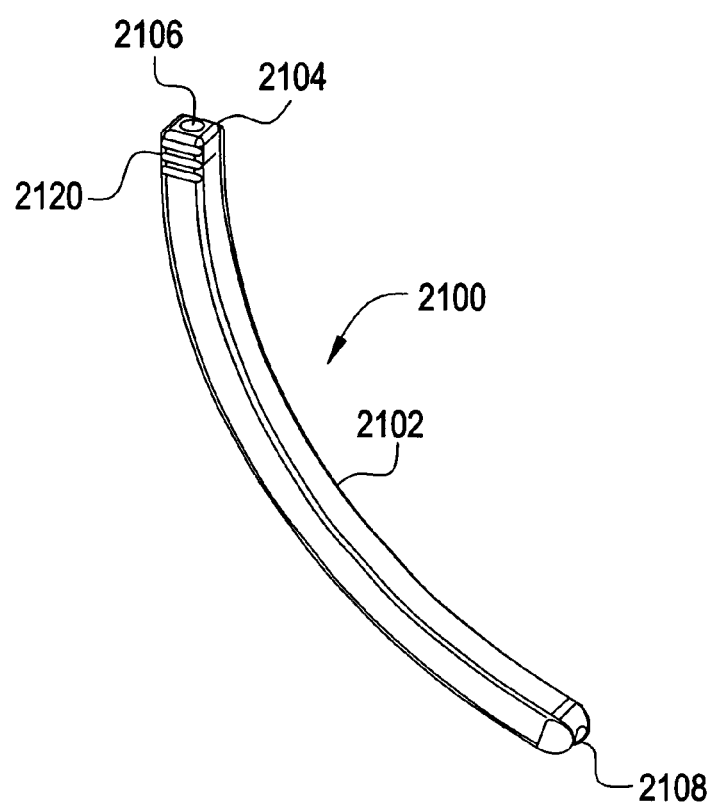
FIG. 21 illustrates an exemplary small dilator, according to some embodiments of the present invention.
Figure 22:
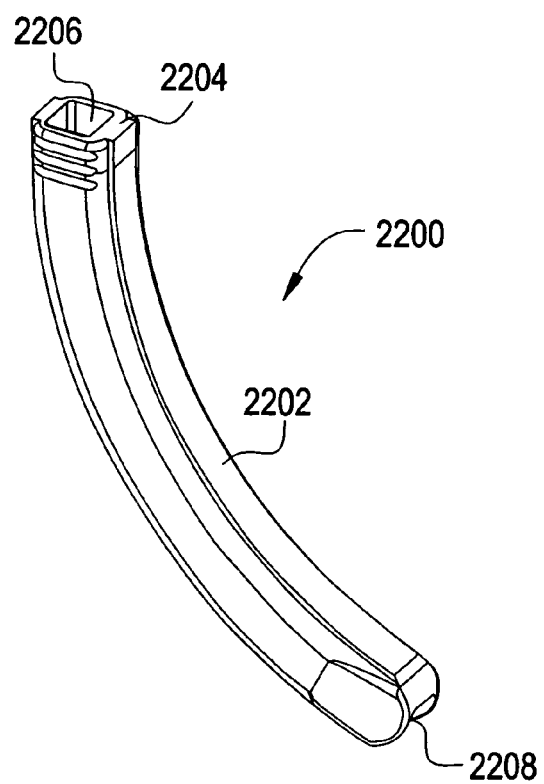
FIG. 22 an exemplary large dilator, according to some embodiments of the present invention.

FIGS. 21-22 illustrate exemplary dilators that are configured to be guided down the barbed trocar 500 (shown in FIG. 5) and between distraction ramps 1502, 1504 using rail/slot 1506. FIG. 21 illustrates an exemplary small dilator 2100, according to some embodiments of the present invention. FIG. 22 an exemplary large dilator 2200, according to some embodiments of the present invention. In some embodiments, the small dilator 2100 is initially guided down over the barbed trocar 500 (shown in FIG. 5) and between the distraction ramps 1502, 1504. Then, the large dilator 2200 is guided down over the small dilator 2100 and also between the distraction ramps 1502, 1504.

Both dilators 2100 and 2200 are further configured to be curved in a similar fashion as the trocar 500 (shown in FIG. 5). The curvature radius of the trocar 500, dilators 2100, 2200, and other instruments discussed in the present application are configured to substantially match in order to prevent wobbling of these instruments when they are being advanced toward the surgical site. In some embodiments, the dilator 2200 can be shorter than the dilator 2100, which can further accommodate placement and removal of the dilators. The dilators can be manufactured from any biocompatible material such as, but not limited to stainless steel, titanium, aluminum, and/or polyetheretherketone ("PEEK"). In some embodiments, the material can be also non-conductive radiolucent material, and can be hammered with a mallet to advance it to the surgical site.

Figure 35:
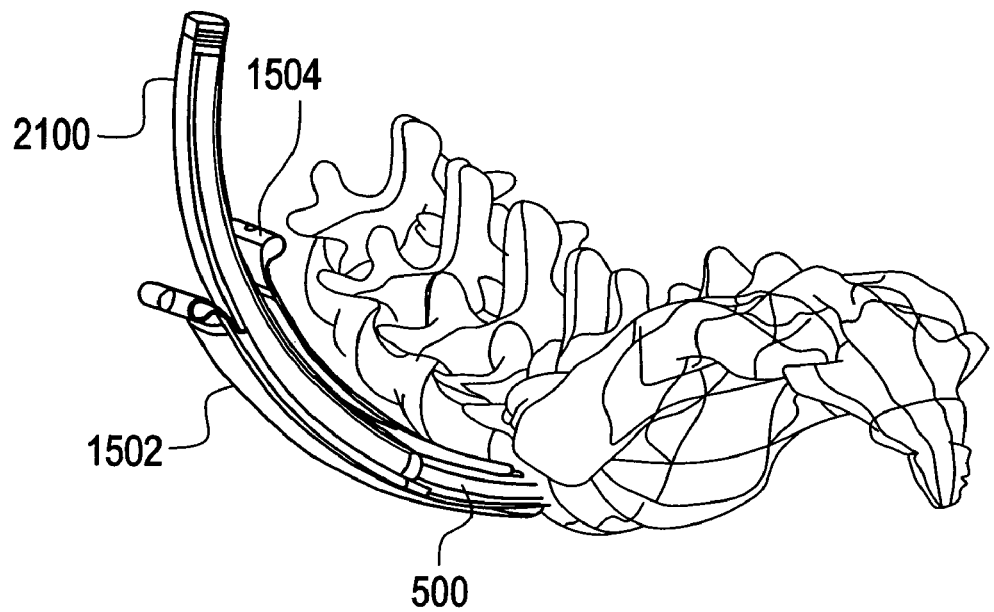
FIG. 35 illustrates the small dilator spreading the tissue distracters, according to some embodiments of the present invention.

Referring to FIG. 21, small dilator 2100 includes a housing 2102 having an open channel 2104. The channel 2104 is sized to accommodate insertion of the trocar 500. The channel 2104 is disposed throughout the interior of the housing 2102 and begins with an opening 2106 at the top (or near the proximal end) of the dilator 2100 and ends with an opening 2108 at the bottom (or near the distal end) of the dilator 2100. The dilator 2100 is configured to be placed over the trocar 500 (shown in FIG. 5) with the opening 2108 and then slid down the trocar 500 until the dilator 2100 reaches the surgical site, as shown in FIG. 35. The housing 2102 of the dilator 2100 further includes a plurality of grasping ribs 2120 disposed near the proximal end of the dilator. The grasping ribs 2120 are further configured to allow holding the dilator 2100 when the dilator is being slid down the trocar 500. As illustrated in FIG. 21, the channel 2104 has a round cross-section in order to accommodate placement of the trocar 500. Further, the dilator 2100 has a square cross-section. As can be understood by one skilled in the art, the cross-sections of the channel 2104 and the dilator 2100 can vary as desired.

Figure 36:
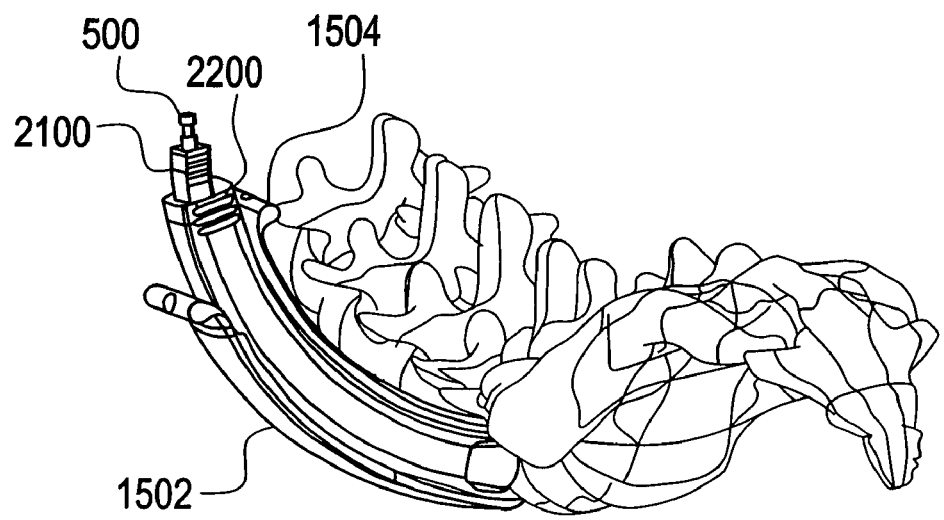
FIG. 36 illustrates the large dilator spreading the tissue distracters over the small dilator, according to some embodiments of the present invention.

Referring to FIG. 22, large dilator 2200 includes a housing 2202 having an open rail/slot 2204. The rail/slot 2204 is sized to accommodate insertion of the small dilator 2100. The rail/slot 2204 is disposed throughout the exterior of the housing 2202 and begins with an opening 2206 at the top (or near the proximal end) of the dilator 2200 and ends with an opening 2208 at the bottom (or near the distal end) of the dilator 2200. The dilator 2200 is configured to be placed over the dilator 2100 (shown in FIG. 21) with the opening 2208 and then slid down the dilator 2100 until the dilator 2200 reaches the surgical site, as shown in FIG. 36. The housing 2202 of the dilator 2200 further includes a plurality of grasping ribs 2220 disposed near the proximal end of the dilator. The grasping ribs 2220 are further configured to allow holding the dilator 2200 when the dilator is being slid down the small dilator 2100. As illustrated in FIG. 22, the rail/slot 2204 has a square rail/slot cross-section in order to accommodate placement of the small dilator 2100. Further, the dilator 2200 has a square cross-section. As can be understood by one skilled in the art, the cross-sections of the rail/slot 2204 and the dilator 2200 can vary as desired.

Figure 23:
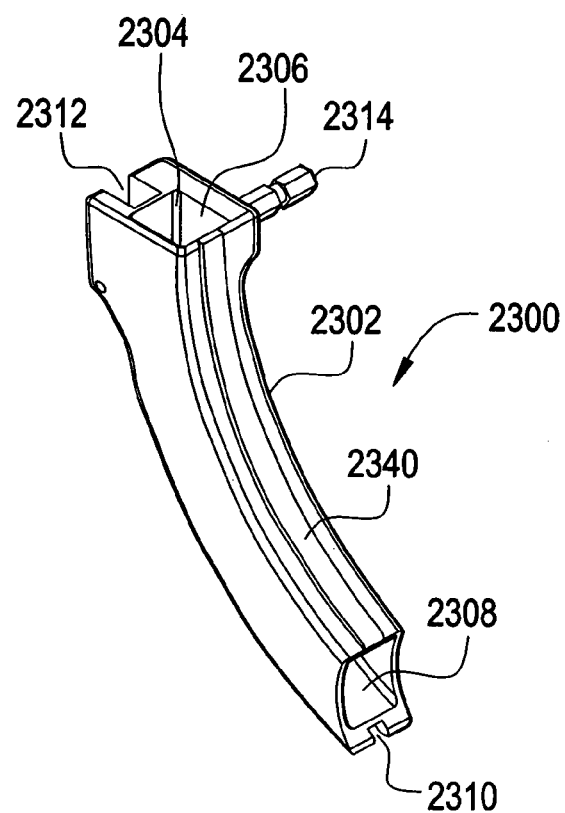
FIG. 23 an exemplary curved portal, according to some embodiments of the present invention.
Figure 24:
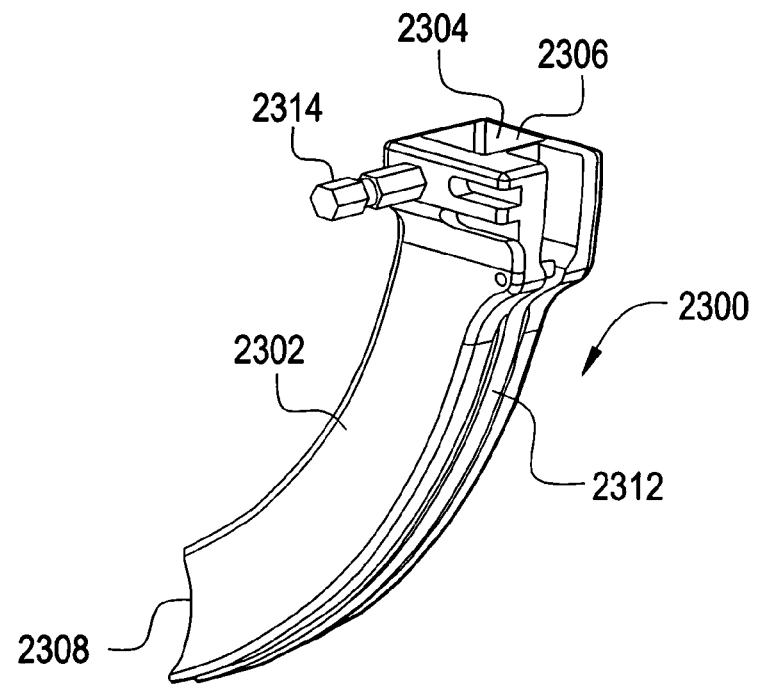
FIG. 24 is another view of the curved portal shown in FIG. 23.
Figure 25:
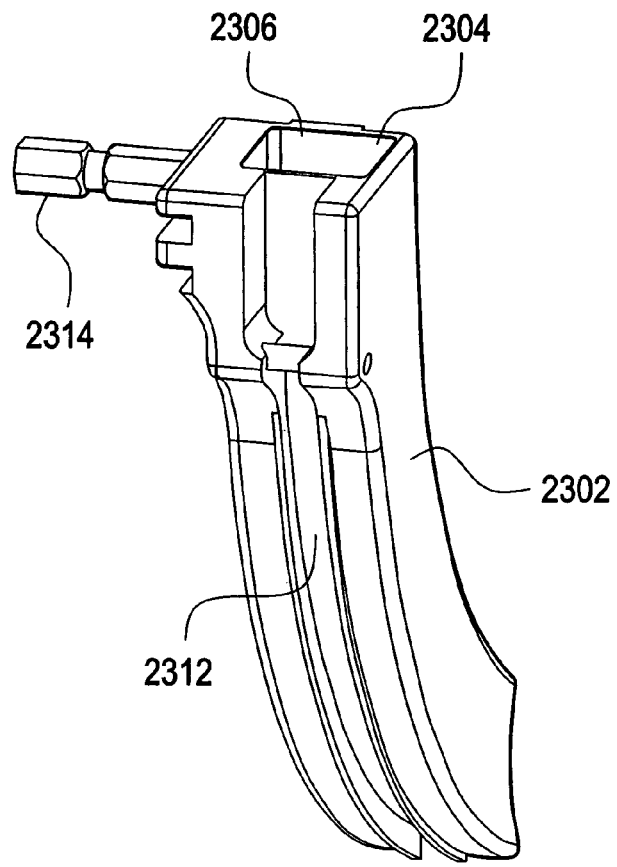
FIG. 25 is a rear view of the curved portal shown in FIG. 23.

FIGS. 23-25 illustrate an exemplary curved portal 2300, according to some embodiments of the present invention. FIG. 23 illustrates the curved portal 2300. FIG. 24 is another view of the curved portal 2300. FIG. 25 is a rear view of the curved portal 2300.

As illustrated in FIGS. 23-25, the portal 2300 includes a housing 2302 disposed between the proximate end 2306 and a distal end 2308. The housing 2302 also includes an interior channel 2304 that is disposed between an opening at the proximate end 2306 and an opening at the distal end 2308. The channel 2304 is sized to accommodate insertion over the large dilator 2200 (shown in FIG. 22) and subsequent instrumentation. Channel 2304 may contain additional rail/slots to aid in guiding instrumentation. The housing 2302 also includes an outside rail/slot 2312 disposed on the rear portion of the working portal 2300, as illustrated in FIGS. 23-25. The rail/slot 2312 is configured to extend through the whole housing 2302 and terminate at the distal end 2308 at an opening 2310. The opening 2310 is further configured to accommodate protrusion of an awl 2600 (shown in FIG. 26) upon its insertion through the rail/slot 2312. The outside rail/slot 2312 and 2340 are configured to accommodate insertion of the working portal 2300 between tissue distracters 1502 and 1504. The outside rail/slot 2312 is also disposed between the proximate end 2306 and the distal end 2308. The distal end 2308 has a curved open end structure that can be configured to accommodate mounting to the lateral wall of the spine.

In some embodiments, the width and/or height of the working portal 2300 can be in the range of 5 mm to 30 mm; alternately, between 10 mm and 25 mm; alternately, between 15 mm and 25 mm; alternately, between 18 mm and 23 mm. In some embodiments, the width of the working portal 2300 can be 20.3 mm. In some embodiments, the height of the portal 2300 can be 24 mm. In some embodiments, the width and/or height of the channel 2304 can be in the range of 5 mm to 30 mm; alternately, between 10 mm and 25 mm; alternately, between 15 mm and 25 mm; alternately, between 18 mm and 23 mm. In some embodiments, the width of the channel 2304 can be 17 mm. In some embodiments, the height of the channel 2304 can be 19 mm. The curvature radius of the working portal 2300 can be in above 3 mm. In some embodiments, the curvature radius of the working portal 2300 can be very large, thereby the working portal 2300 having only a slightly curved shape. In some embodiments, the curvature radius of the working portal 2300 is 12 cm.

Figure 44A:
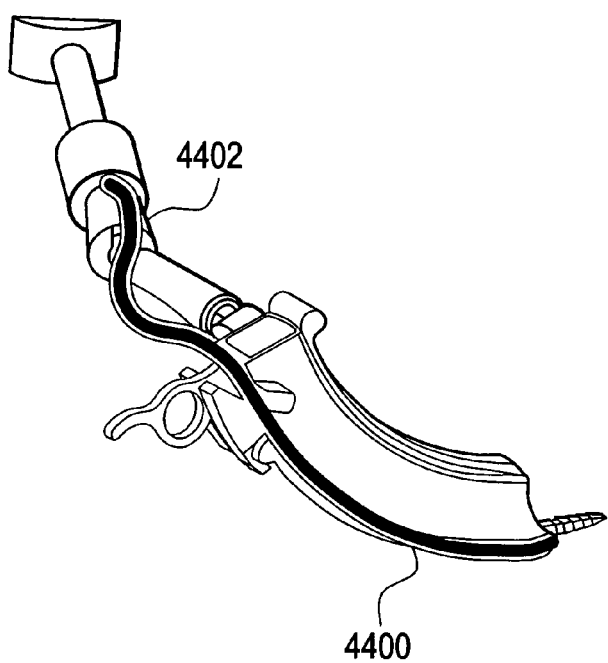
FIGS. 44a-c illustrate an exemplary working portal with an endoscope, displaying the endoscope's field of view, according to some embodiments of the present invention.
Figure 44B:
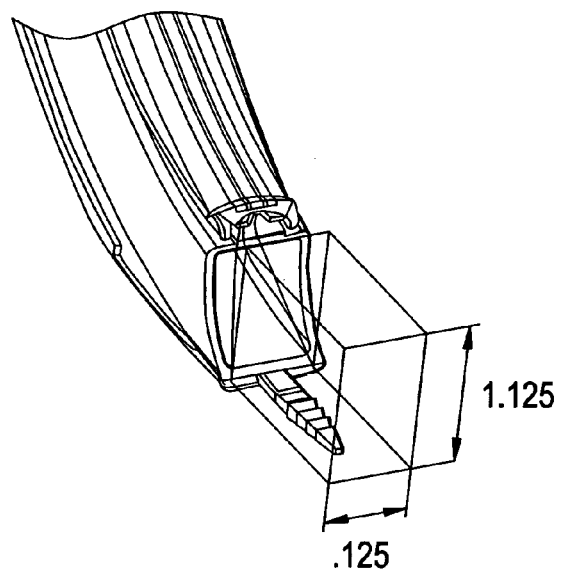
Figure 44C:
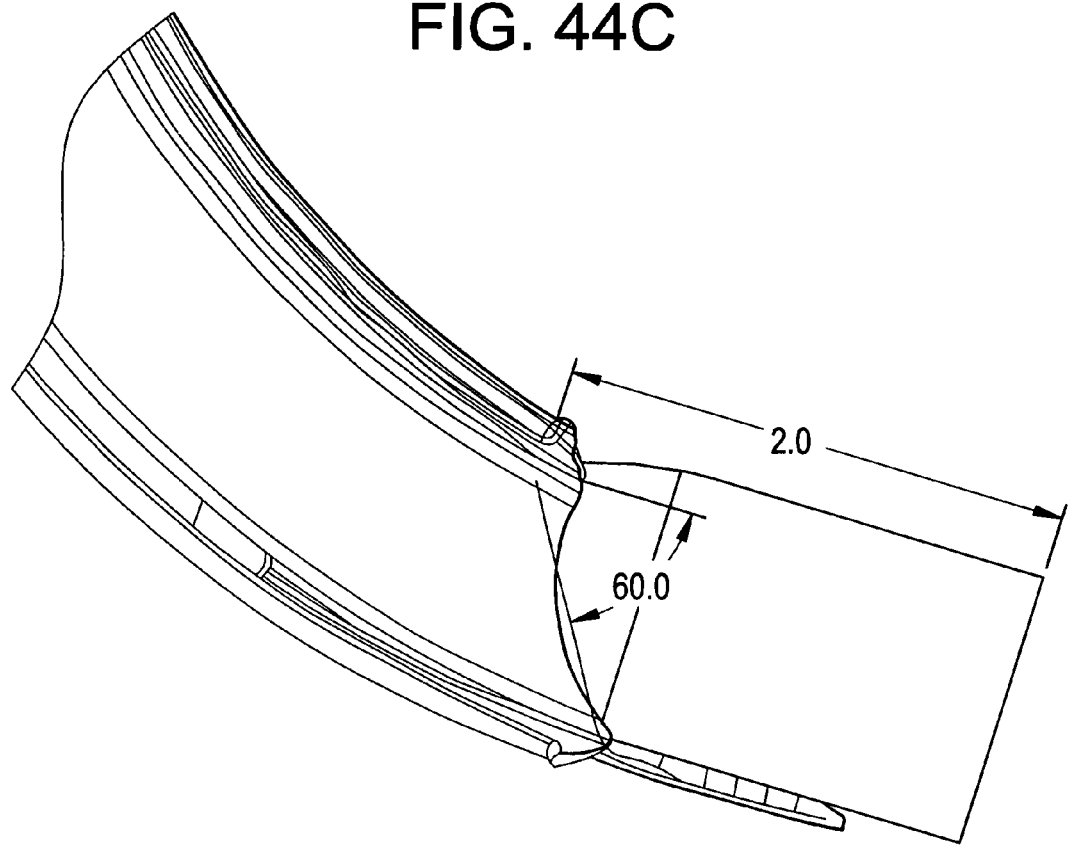

In some embodiments, the working portal 2300 can also accommodate placement of an endoscope 4400 that allows viewing of the surgical area, as illustrated in FIG. 44a-c. Direct visualization is via a flexible or fixed radius endoscope. Intra-operative electrophysiological monitoring and fluoroscopy are utilized. The endoscope 4400 can be disposed along one of the walls of the working portal 2300, as shown in FIG. 44a, and can be mounted on the holding arm 4402 that secures the working portal 2300. As illustrated in FIGS. 44b-c, the endoscope viewing area can be on the order of about 50.8 mm by 15.875 mm by 28.575 mm. FIG. 44c illustrates the field of view of the endoscope.

Referring back to FIGS. 23-25, the working portal 2300 can be configured to have a substantially square or rectangular cross-section. As can be understood by one skilled in the art, the cross-section of the working portal 2300 can have any other shape, e.g., elliptical, round, polygonal, or any other desired shape. Because of the curvature of the working portal 2300, it can accommodate insertion of an implant at a direction that is substantially perpendicular to the surface of the body of the patient. Once the implant is inserted at the proximate end of the working portal 2300, it is advanced toward the surgical site down the interior channel of the working portal 2300. Upon approaching the surgical site, the direction of movement of the implant changes from substantially perpendicular or angular with regard to the body of the patient to substantially lateral or transverse. This allows the surgeon easily manipulate insertion and placement of the implant without having to create a large incision in the patient. The working portal 2300 can be configured to accommodate insertion of an implant having the following dimensions: height in the range of 8 mm to 18 mm, an anterior-posterior depth of in the range of 8 mm to 30 mm (alternately, between 10 mm to 25 mm; alternately, between 15 mm to 25 mm; alternately, between 18 mm to 23 mm; in some embodiments, the depth can be approximately 22 mm), and a lateral width in the range of 20 mm to 70 mm (alternately, between 30 mm to 65 mm; alternately, between 40 mm to 50 mm; alternately, between 45 mm to 55 mm).

In some embodiments, the working portal 2300 can be manufactured from any biocompatible material such as, but not limited to stainless steel, titanium, aluminum, and/or PEEK. As can be understood by one skilled in the art, the portal 2300 can be manufactured from any other suitable material(s).

Figure 37:
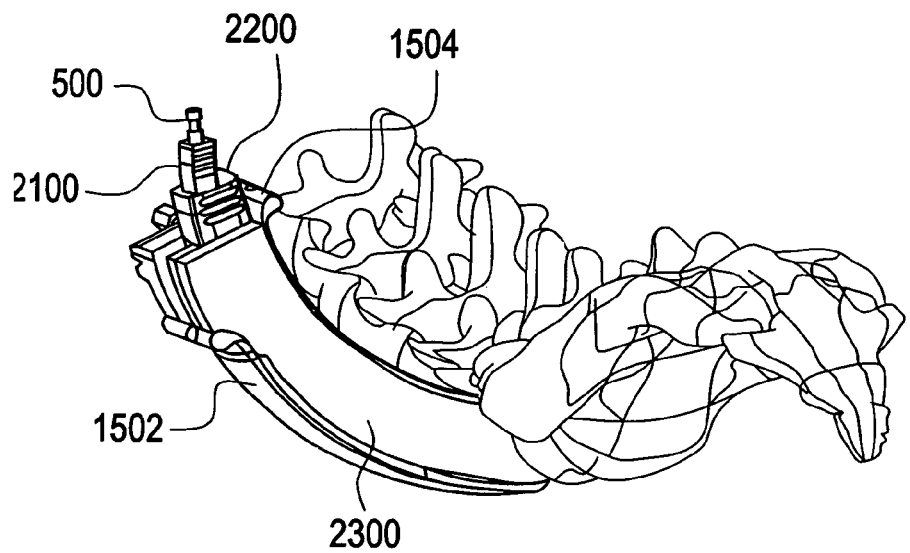
FIG. 37 illustrates the portal sliding over the dilators, according to some embodiments of the present invention.
Figure 38:
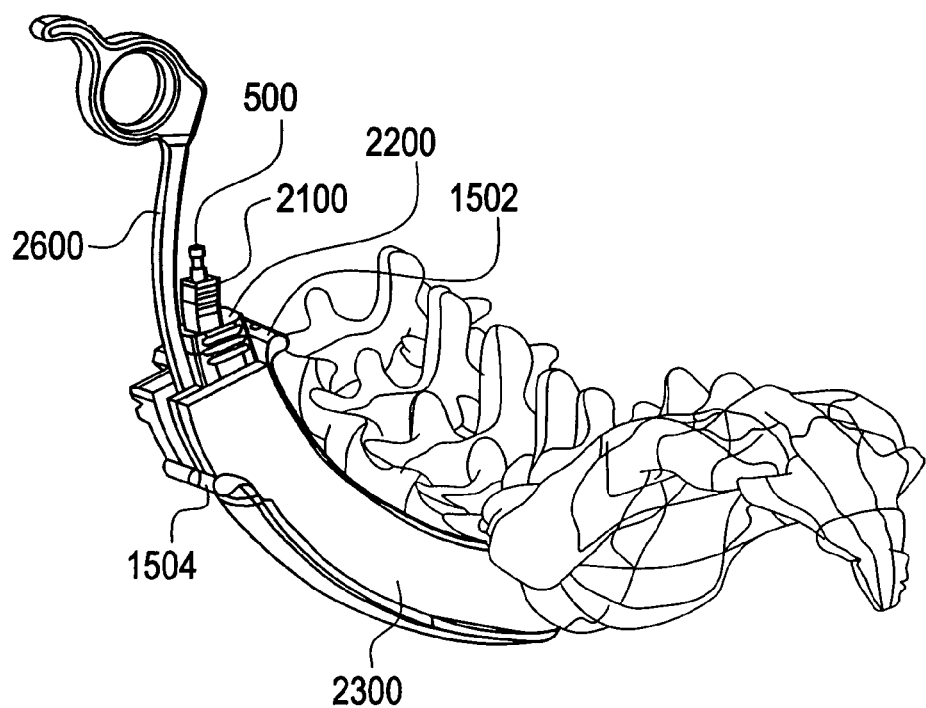
FIG. 38 illustrates the anterior awl securing the portal, according to some embodiments of the present invention.
Figure 39:
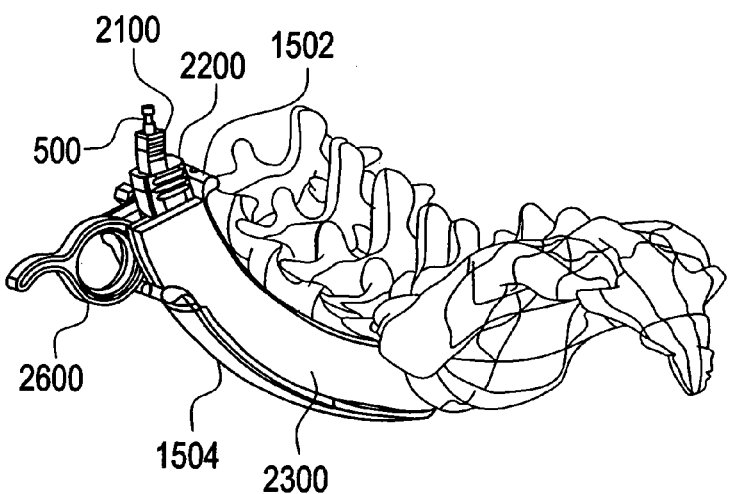
FIG. 39 illustrates the anterior awl being fully seated, according to some embodiments of the present invention.
Figure 40:
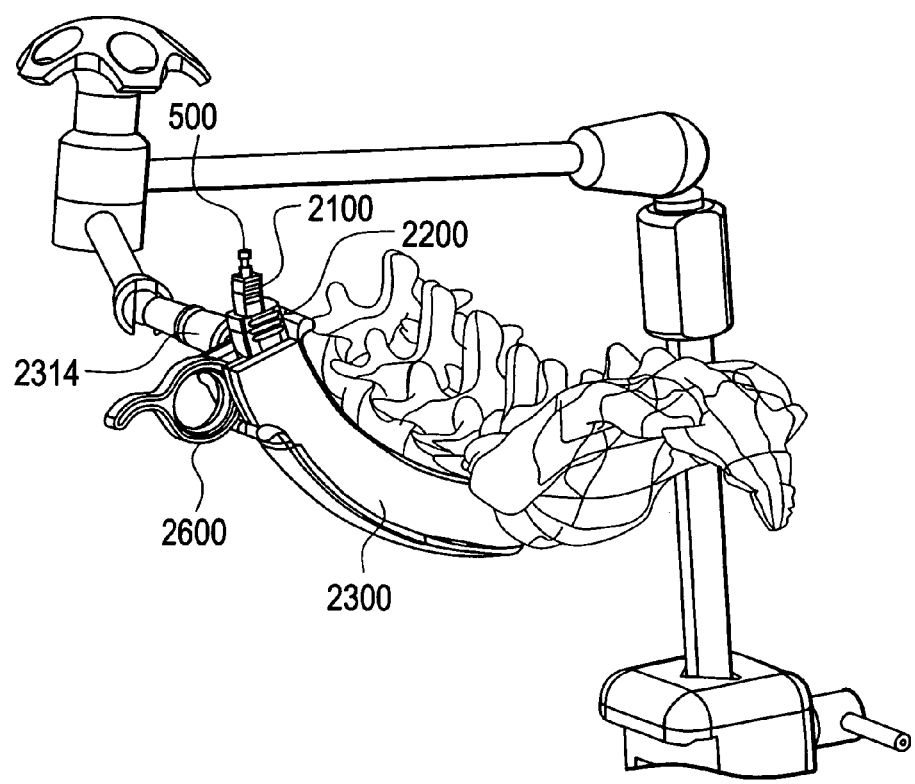
FIG. 40 illustrates an exemplary stabilization arm being mounted to the portal, according to some embodiments of the present invention.

Once the portal 2300 is satisfactorily located and its location is verified via x-ray (or any other means), an anterior awl 2600 can be inserted within outer slot/rail 2312 to secure the working portal 2300 to the spine. FIG. 37 illustrates the portal 2300 prior to insertion of anterior awl 2600. As shown in FIG. 37, along with the portal 2300, the trocar 500, the dilators 2100 and 2200, and the ramps 1502 and 1504 are also inserted. The awl 2600 contains a handle configured to protrude away from the distal end 2308 of the portal 2300 (as shown in FIGS. 38-39).

Figure 26:
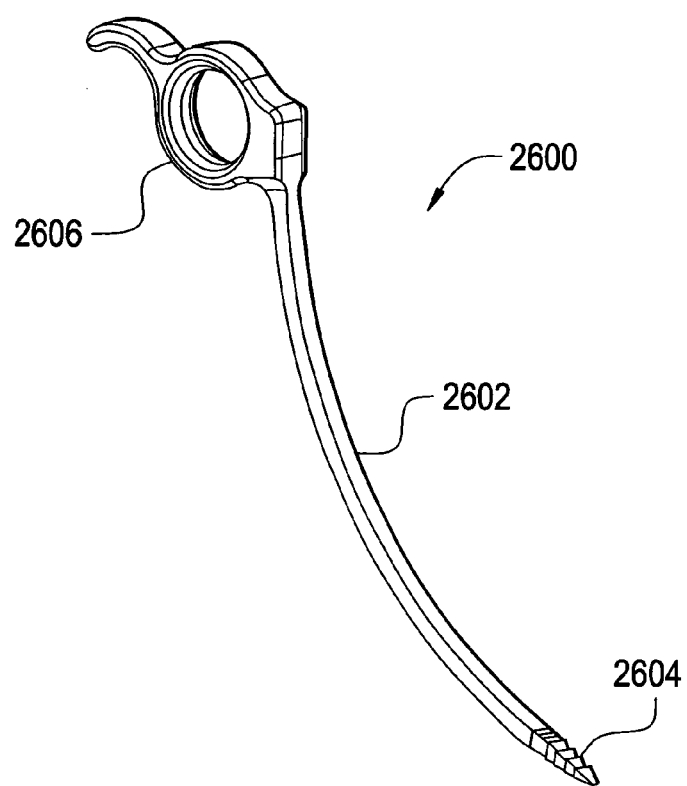
FIG. 26 illustrates an exemplary anterior awl, according to some embodiments of the present invention.

Referring to FIG. 26, the awl 2600 includes a curved shaft 2602 disposed between a handle 2606 at the proximate end of the awl 2600 and a barbed tip 2604 at the distal end of the awl 2600. The barbed tip 2604 is configured to make an incision in the vertebral wall. The shaft 2602 is configured to be curved in a similar fashion as other instruments (e.g., the trocars, dilators, etc.) in order to allow adequate advancement of the awl 2600 towards the surgical site. In some embodiments, the awl 2600 is manufactured from any biocompatible material such as, but not limited to stainless steel, titanium, aluminum, and/or PEEK. In some embodiments, the material can be also a radio-opaque material. As can be understood by one skilled in the art, the awl 2600 can be manufactured from any other suitable materials.

Figure 41:
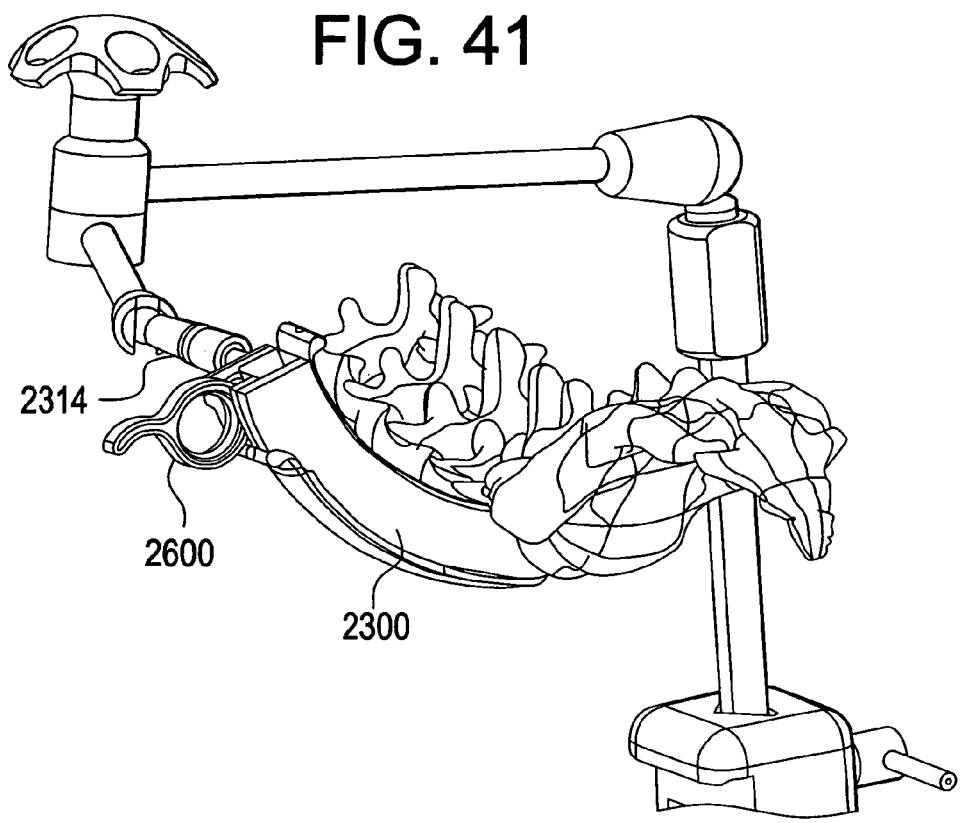
FIG. 41 illustrates an exemplary portal assembly with dilators and trocar being removed, according to some embodiments of the present invention.
Figure 42:
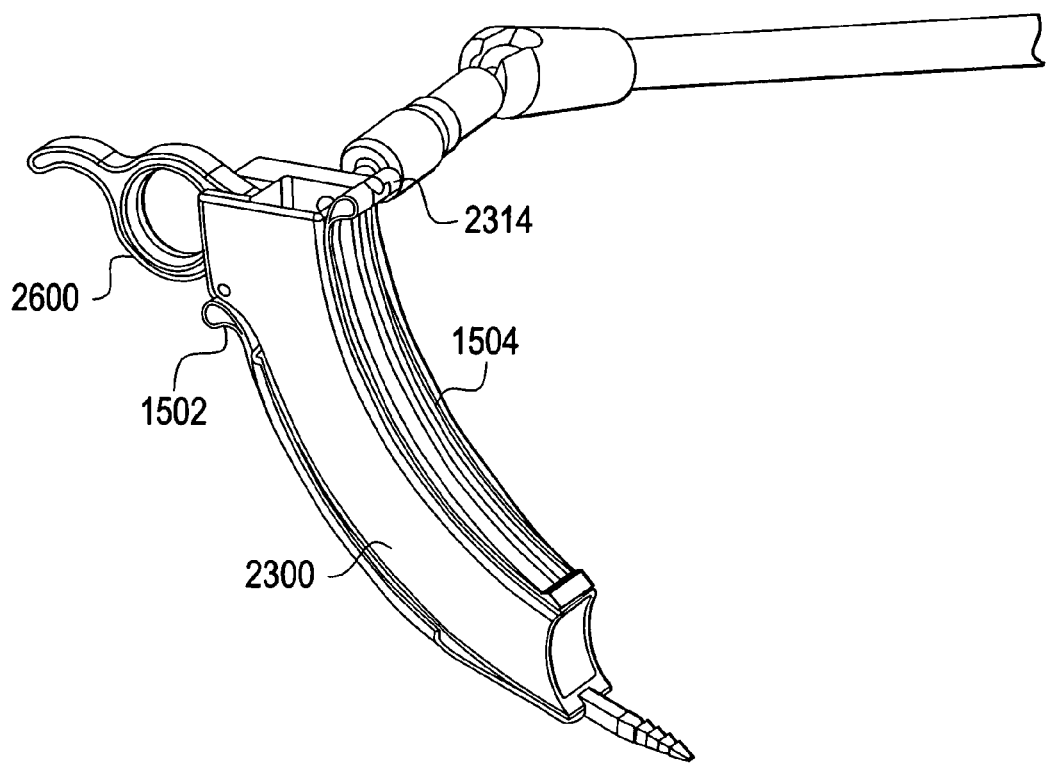
FIG. 42 illustrates an exemplary final portal assembly and a protrusion of the anterior awl, according to some embodiments of the present invention.

The working portal construct can be further stabilized using a stabilization arm 2314 (e.g., StrongArm, manufactured by Mediflex). The arm 2314 is coupled to a stationary equipment in the operating room, such as the operating table. As can be understood by one skilled in the art, any other holding arms can be used. Once the portal is docked using the anterior awl and stabilization arm, the dilators 2100, 2200 and the trocar 500 are removed, thereby leaving the working portal 2300 and the barbed awl 2600 allowing the surgeon to perform desired procedures (e.g., delivery of an implant), as shown in FIGS. 41-42.

In some embodiments, where the present invention's device and instrumentation are used for implant delivery, the implants may include, but are not limited to: bone screws, plates, interbody devices, artificial discs, or any other implants. Further, the present invention's device and methodology can be used in any number of surgical procedures, including nucleus replacement, total disc replacement, interbody fusion, discectomy, neural decompression, implant delivery (whether for fixation purposes and/or stabilization), or any other procedure.

Example embodiments of the methods and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed is:

1. A device for performing a procedure on the spine of a patient, comprising:
   a working portal configured to be advanced toward a surgical site of the spine of the patient;
   said working portal comprising:
      a distal end and a proximate end;
      a working portal housing having an interior channel disposed between said distal end and said proximate end;
      said distal end is configured to be disposed at the surgical site and said proximate end is disposed away from said surgical site;
      said working portal housing has a curved shape defined between said proximate end and said distal end;
   an exterior channel disposed on an outside surface of said working portal housing and between said distal end and said proximate end; and
   an anterior awl configured to be advanced toward the surgical site along said exterior channel and further configured to anchor said working portal at the surgical site,
   wherein said working portal is configured to allow advancement of at least one surgical tool and/or at least one implant toward the surgical site.

2. The device according to claim 1, wherein said proximate end is disposed at an angle with respect to said distal end.

3. The device according to claim 1, further comprising a holding arm configured to stabilize said working portal during the surgical procedure.

4. The device according to claim 1, wherein the working portal has a width of in a range of 5 mm to 30 mm and a height in a range of 5 mm to 30 mm.

5. The device according to claim 1, wherein the working portal is configured to accommodate insertion of an implant having a height in the range of 8 mm to 18 mm, an anterior-posterior depth in a range of 8 mm to 30 mm, and a lateral width in the range of 20 mm to 70 mm.

6. The device according to claim 1, wherein the working portal has a cross-section selected from group consisting of: square, rectangular, oval, polygonal.

7. The device according to claim 1, wherein the working portal further comprises an endoscope for viewing the surgical area.

8. The device according to claim 1, wherein the working portal is used to deliver an implant, wherein the implant is selected from a group consisting of: a bone screw, a plate, an interbody device, an artificial disc, and any other spinal device.

9. A method for performing a surgical procedure on the spine of a patient, the method comprising:
   advancing a working portal toward a surgical site located at the spine of the patient;
   the working portal comprising:
      a distal end and a proximate end;
      a working portal housing having an open interior channel disposed between the distal end and the proximate end;
      the distal end is configured to be disposed at the surgical site and the proximate end is disposed away from the surgical site;
      the housing has a curved shape defined between the proximate end and the distal end, wherein the proximate end is disposed at an angle with respect to the distal end;
   advancing at least one surgical tool and/or at least one implant toward the surgical site via the working channel to perform the procedure;
   advancing an anterior awl toward the surgical site along an exterior channel disposed on an outside surface of the working portal housing; and
   anchoring the working portal at the surgical site.

10. The method according to claim 9, further comprising stabilizing the working portal during the surgical procedure using a holding arm.

11. The method according to claim 9, wherein the working portal has a cross-section selected from group consisting of: square, rectangular, oval, polygonal.

12. The method according to claim 9, wherein the working portal further comprises an endoscope for viewing the surgical area.

13. The method according to claim 9, further comprising delivering an implant through the working portal, wherein the implant is selected from a group consisting of: a bone screw, a plate, an interbody device, an artificial disc, and any other spinal device.

14. A system for performing a spinal procedure comprising:
   a curved trocar guide having a curved channel positionable within a surgical site relative to a vertebral body;
   a curved cutting trocar that slides inside the curved channel to cut an opening in a wall of the vertebral body;
   a curved docking trocar that slides inside the curved channel to anchor to the vertebral body;

a curved tissue separator that advances along the curved docking trocar to remove tissue from the surgical site;

a curved tissue distracter that advances along the curved docking trocar to the vertebral body after the curved tissue separator is removed;

a curved dilator that advances through the curved tissue distracter to the vertebral body to enlarge the surgical site;

a curved working portal that advances over the curved dilator to the vertebral body to create a working portal in the surgical site; and an awl that secures the curved working portal to the vertebral body.

15. The system of claim 14, further comprising a plurality of dilators of increasing cross-sectional area that gradually enlarge the surgical site prior to insertion of the curved working portal.

16. The system of claim 14, wherein the awl advances within an exterior channel of the curved working portal and couples a distal end of the curved working portal to the vertebral body.

17. A method for performing a spinal procedure comprising:

positioning a curved trocar guide having a curved channel within a surgical site relative to a vertebral body;

sliding a curved cutting trocar inside the curved channel to cut an opening in a wall of the vertebral body;

sliding a curved docking trocar inside the curved channel to anchor to the vertebral body;

advancing a curved tissue separator along the curved docking trocar to remove tissue from the surgical site;

advancing a curved tissue distracter along the curved docking trocar to the vertebral body after removing the curved tissue separator;

advancing a curved dilator through the curved tissue distractor to the vertebral body to enlarge the surgical site;

advancing a curved working portal over the curved dilator to the vertebral body to create a working portal in the surgical site; and securing the curved working portal to the vertebral body.

18. The method of claim 17, further comprising delivering an implant through the curved working portal to the vertebral body.

* * * * *